(12) United States Patent
Fang et al.

(10) Patent No.: US 7,498,024 B2
(45) Date of Patent: *Mar. 3, 2009

(54) COMPOSITIONS AND METHODS FOR ENHANCED EXPRESSION OF IMMUNOGLOBULINS FROM A SINGLE VECTOR USING A PEPTIDE CLEAVAGE SITE

(75) Inventors: Jianmin Fang, Foster City, CA (US); Karin Jooss, Bellevue, WA (US); Jing-Jing Qian, Foster City, CA (US)

(73) Assignee: Cell Genesys, Inc., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/831,302

(22) Filed: Apr. 26, 2004

(65) Prior Publication Data

US 2005/0003482 A1    Jan. 6, 2005

Related U.S. Application Data

(63) Continuation-in-part of application No. 10/452,253, filed on Jun. 3, 2003.

(60) Provisional application No. 60/540,554, filed on Feb. 2, 2004.

(51) Int. Cl.
  C12N 7/01   (2006.01)
  C12N 15/00  (2006.01)
  C12N 15/11  (2006.01)
  C12N 15/13  (2006.01)
  C12N 5/10   (2006.01)
  C12P 21/00  (2006.01)
  C12P 21/08  (2006.01)

(52) U.S. Cl. ............... 424/93.2; 435/320.1; 435/69.1; 435/325; 435/326; 536/24.1

(58) Field of Classification Search ............ None
See application file for complete search history.

(56) References Cited

U.S. PATENT DOCUMENTS

| | | | |
|---|---|---|---|
| 5,436,146 A | 7/1995 | Shenk et al. | |
| 5,643,745 A | 7/1997 | Stuart | |
| 5,686,279 A | 11/1997 | Finer et al. | |
| 5,753,500 A | 5/1998 | Shenk et al. | |
| 5,846,767 A | 12/1998 | Halpin et al. | |
| 5,863,765 A | 1/1999 | Berry et al. | |
| 5,872,005 A | 2/1999 | Wang et al. | |
| 5,994,106 A | 11/1999 | Kovesdi et al. | |
| 6,040,183 A | 3/2000 | Ferrari et al. | |
| 6,093,570 A | 7/2000 | Ferrari et al. | |
| 6,127,175 A | 10/2000 | Vigne et al. | |
| 6,133,028 A | 10/2000 | Imler et al. | |
| 6,180,371 B1 | 1/2001 | Lollar | |
| 6,200,560 B1 | 3/2001 | Couto et al. | |
| 6,221,349 B1 | 4/2001 | Couto et al. | |
| 6,251,632 B1 | 6/2001 | Lillicrap et al. | |
| 6,271,025 B1 | 8/2001 | Negrier et al. | |
| 6,320,029 B1 | 11/2001 | Miekka et al. | |
| 6,331,415 B1 | 12/2001 | Cabilly et al. | |
| 6,358,703 B1 | 3/2002 | Cho et al. | |
| 6,376,463 B1 | 4/2002 | Lollar | |
| 6,458,563 B1 | 10/2002 | Lollar | |
| 6,517,830 B1 | 2/2003 | Lollar et al. | |
| 6,518,482 B2 | 2/2003 | Lubon et al. | |
| 6,548,286 B1 | 4/2003 | Samulski et al. | |
| 6,599,724 B1 | 7/2003 | Mikaelsson et al. | |
| 6,602,503 B1 | 8/2003 | Lobb et al. | |
| 6,623,940 B1 | 9/2003 | Ledbetter et al. | |
| 6,632,800 B1 | 10/2003 | Russell et al. | |
| 6,642,028 B1 | 11/2003 | Ill et al. | |
| 6,649,375 B2 | 11/2003 | Connelly et al. | |
| 6,692,736 B2 | 2/2004 | Yu et al. | |

(Continued)

FOREIGN PATENT DOCUMENTS

EP        0623679 A1    11/1994

(Continued)

OTHER PUBLICATIONS

Paulus, H. Protein splicing: A novel form of gene expression and paradigm for self-catalyzed protein rearrangements, Pure and Appl. Chem, 1998, vol. 70 (1), pp. 1-8.*
Landry, Dr. Immunoglobulin Structure, last modified Oct. 11, 2000, downloaded Dec. 5, 2007.*
Herzenberg, et al., Eds., "Immunochemistry and Molecular Immunology", vol. 1, 5th ed., Weir's Handbook of Experimental Immunology, 1986.
Miller, et al., Eds., "Gene Transfer Vectors for Mammalian Cells", Current Communications in Molecular Biology, 1987.
Ausubel, et al., Eds., Current Protocols in Molecular Biology, vol. 1, 1987.
Mullis, et al., PCR: The Polymerase Chain Reaction, 1994.
Coligan, et al., Eds., Current Protocols in Immunology, vol. 1, 1991.
Zufferey, et al., "Mutiply Attenuated Lentiviral Vector Achieves Efficient Gene Delivery In Vivo", Nat. Biotechnol., vol. 15, pp. 871-875, 1997.

(Continued)

*Primary Examiner*—Maria B Marvich
(74) *Attorney, Agent, or Firm*—Ropes & Gray LLP; James F. Haley, Jr.; Teresa Chen

(57) ABSTRACT

Single vector constructs for expression of an immunoglobulin molecule or fragment thereof and methods of making and using the same are described. The vectors comprise a self-processing cleavage sequence between a first and second immunoglobulin coding sequence allowing for expression of a functional antibody molecule using a single promoter. The vector constructs include the coding sequence for a self-processing cleavage site and may further include an additional proteolytic cleavage sequence which provides a means to remove the self processing peptide sequence from an expressed immunoglobulin molecule or fragment thereof. The vector constructs find utility in methods for enhanced production of biologically active immunoglobulins or fragments thereof in vitro or in vivo.

28 Claims, 14 Drawing Sheets

U.S. PATENT DOCUMENTS

| | | | |
|---|---|---|---|
| 6,911,200 | B2 | 6/2005 | Yu et al. |
| 6,933,362 | B1 | 8/2005 | Belfort et al. |
| 7,001,596 | B1 | 2/2006 | Johnson et al. |
| 2002/0168339 | A1 | 11/2002 | Piechaczyk et al. |
| 2002/0168342 | A1 | 11/2002 | Wang et al. |
| 2003/0068307 | A1 | 4/2003 | Yu et al. |
| 2003/0083290 | A1 | 5/2003 | Kingsman et al. |
| 2003/0099616 | A1 | 5/2003 | Irving et al. |
| 2003/0099932 | A1 | 5/2003 | Lorens et al. |
| 2004/0086485 | A1 | 5/2004 | Aguilar-Cordova |
| 2004/0131591 | A1 | 7/2004 | Kingsman et al. |
| 2004/0209830 | A1* | 10/2004 | Russell et al ............... 514/44 |
| 2004/0235011 | A1* | 11/2004 | Cooper et al. ............... 435/6 |
| 2004/0265955 | A1 | 12/2004 | Fang |
| 2005/0042721 | A1 | 2/2005 | Fang |
| 2005/0095705 | A1 | 5/2005 | Kadan et al. |
| 2006/0228336 | A1 | 10/2006 | Ko |
| 2007/0275915 | A1 | 11/2007 | Hallenbeck et al. |

FOREIGN PATENT DOCUMENTS

| | | |
|---|---|---|
| WO | WO 95-21249 A | 8/1995 |
| WO | WO97/49725 | 12/1997 |
| WO | WO99/46274 | 9/1999 |
| WO | WO99/46299 | 9/1999 |
| WO | WO99/61595 | 12/1999 |
| WO | WO99/61642 | 12/1999 |
| WO | WO00/23116 | 4/2000 |
| WO | WO00/71141 | 11/2000 |
| WO | WO01/03726 | 1/2001 |
| WO | WO01/27303 | 4/2001 |
| WO | WO01/45510 | 6/2001 |
| WO | WO01/68109 | 9/2001 |
| WO | WO 01-70763 A | 9/2001 |
| WO | WO02/24723 | 3/2002 |
| WO | WO02/072023 | 9/2002 |
| WO | WO03/031598 | 4/2003 |
| WO | WO03/047507 | 6/2003 |
| WO | WO03/080108 | 10/2003 |
| WO | WO03/087161 | 10/2003 |
| WO | WO03/100053 | 12/2003 |
| WO | WO 2004/092348 | 10/2004 |

OTHER PUBLICATIONS

Dull, et al., "A Third Generation Lentivirus Vector with a Conditional Packaging System", J. Virol., vol. 72, No. 11, pp. 8463-8471, 1998.

Jackson, et al., Trends Biochem., Sci., vol. 15, No. 12, pp. 477-483, 1990.

Jackson, et al., "Internal Initiation of Translation in Eukaryotes: The Picornavirus Paradigm and Beyond", RNA, vol. 1, No. 10, pp. 985-1000, 1995.

Kohler, et al., "Derivation of Specific Antibody-Producing Tissue Culture and Tumor Lines by Cell Fusion", Eur. J. Immunol., vol. 6, pp. 511-519, 1976.

Huez, et al., "Two Independent Internal Ribosome Entry Sites are Involved in Translation Initiation of Vascular Endothelial Growth Factor mRNA", Mol. Cell. Biol., vol. 18, No. 11, pp. 6178-6190, 1998.

Duke, et al., "Sequence and Structural Elements that Contribute to Efficient Encephalomyocarditis Virus RNA Translation", J. Virol, vol. 66, No. 3, pp. 1602-1609, 1992.

Jang, et al., "Cap-Independent Translation of Encephalomyocarditis Virus RNA: Structural Elements of the Internal Ribosomal Elements of the Internal Ribosomal Entry Site and Involvement of a Cellular 57kD RNA-Binding Protein", Gene Dev., vol. 4, pp. 1560-1572, 1990.

Borman, et al., "Sequences within the Poliovirus Internal Ribosome Entry Segment Control Viral RNA Synthesis", EMBO J., vol. 13, No. 13, pp. 3149-3157, 1994.

Glass, et al., "Indentification of the Hepatitis A Virus Internal Ribosome Entry Site: In Vivo and In Vitro Analysis of Bicistronic RNAs Containing the HAV 5' Noncoding Region", Virol., vol. 193, pp. 842-852, 1993.

Freshney, Ed., Animal Cell Culture, 1987.

Sambrook, et al., "Molecular Cloning: A Laboratory Manual", Cold Spring Laboratory Press, 2nd Ed., 1989.

Gait, Ed., Oligonucleotide Synthesis, 1984.

Tsukiyama-Kohara, et al., "Internal Ribosome Entry Site within Hepatitis C Virus RNA", J. Virol., vol. 66, No. 3, pp. 1476-1483, 1992.

Frolov, et al., "*cis*-Acting RNA Elements Required for Replication of Bovine Viral Diarrhea Virus-Hepatitis C Virus 5' Nontranslated Region Chimeras", RNA, vol. 4, pp. 1418-1435, 1998.

Torrent, et al., "Stable MLV-VL30 Dicistronic Retroviral Vectors with a VL30 or MoMLV Sequence Promoting Both Packaging of Genomic RNA and Expression of the 3' Cistron", Hum. Gene Ther., vol. 7, pp. 603-612, 1996.

Van der Velden, et al., "The Role of the 5' Untranslated Region of an mRNA in Translation Regulation During Development", Int. J. Biochem. & Cell Biol., vol. 31, pp. 87-106, 1999.

Macejak, et al., "Internal Initiation of Translation Mediated by the 5' Leader of a Cellular mRNA", Nature, vol. 353, pp. 90-94, 1991.

Oh, et al., "Homeotic Gene *Antennapedia* mRNA Contains 5'-Noncoding Sequences that Confer Translational Initiation by Internal Ribosome Binding", Gene and Dev., vol. 6, pp. 1643-1653, 1992.

Vagner, et al., "Alternative Translation of Human Fibroblast Growth Factor 2 mRNA Occurs by Internal Entry of Ribosomes", Mol. Cell Biol., vol. 15, No. 1, pp. 35-44, 1995.

Berstein, et al., "PDGF2/*c-sis* mRNA Leader Contains a Differentiation-Linked Internal Ribosomal Entry Site (D-IRES)", J. Biol. Chem., vol. 272, No. 14, pp. 9356-9362, 1997.

Teerink, et al., "The Human Insulin-Like Growth Factor II Leader I Contains an Internal Ribosomal Entry Site", Biochim Biophys. Acta, vol. 1264, pp. 403-408, 1995.

Gan, et al., "Internal Initiation of Translation Directed by the 5'-Untranslated Region of the mRNA for eIF4G, a Factor Involved in the Picornovirus-induced Switch from Cap-dependent to Internal Initiation", J. Biol. Chem., vol. 271, No. 2, pp. 623-626, 1996.

Stein, et al., "Translation of Vascular Endothelial Growth Factor mRNA by Internal Ribosome Entry: Implications for Translation under Hypoxia", Mol. Cell. Biol., vol. 18, No. 6, pp. 3112-3119, 1998.

Maga, et al., "*Leishmania* RNA Virus 1-Mediated Cap-dependent Translation", Mol. Cell. Biol., vol. 15, No. 9, pp. 4884-4889, 1995.

Lopez-Lastra, et al., "Characterization of an Internal Ribosomal Entry Segment Within the 5' Leader of Avian Reticuloendotheliosis Virus Type A RNA and Development of Novel MLV-REV-Based Retroviral Vectors", Hum. Gene Ther., vol. 8, pp. 1855-1865, 1997.

Palmenberg, "Proteolytic Processing of Picornoviral Polyprotein", Ann. Rev., Microbiol., vol. 44, pp. 603-623, 1990.

Donnelly, et al., "The 'Cleavage' Activities of Foot-and-Mouth Disease Virus 2A Site-Directed Mutants and Naturally Occurring '2A-Like' Sequences", J. Gen. Virol., vol. 82, pp. 1027-1041, 2001.

Smith, et al., "Comparison of Biosequences", Adv. Appl. Math.., vol. 2, pp. 482-489, 1981.

Needleman, et al., "A General Method Applicable to the Search for Similarities in the Amino Acid Sequence of Two Proteins", J. Mol. Biol., vol. 48, pp. 443-453, 1970.

Pearson, et al., "Improved Tools for Biological Sequence Comparison", Proc. Natl. Acad. Sci. USA, vol. 85, pp. 2444-2448, 1988.

Altschul, et al., "Basic Local Alignment Search Tool", J. Mol. Biol., vol. 215, pp. 403-410, 1990.

National Center for Biotechnology Information (http://www.ncbi.nlm.nih.gov/).

Southern, et al., "Transformation of Mammalian Cells to Antibiotic Resistance with a Bacterial Gene Under Control of the SV40 Early Region Promoter", J. Mol. Appl. Genet., vol. 1, No. 4, pp. 327-341, 1982.

Mulligan, et al., "Expression of a Bacterial Gene in Mammalian Cells", Science, vol. 209, pp. 1422-1427, 1980.

Sugden, et al., "A Vector that Replicates as a Plasmid and Can Be Efficiently Selected in B-Lymphoblasts Transformed by Epstein-Barr Virus", Mol. Cell. Biol., vol. 5, No. 2, pp. 410-413, 1985.

Hitt, et al., "Adenovirus Vectors for Human Gene Therapy", Adv. Virus Res., vol. 55, pp. 479-505, 2000.

Kotin, "Prospects for the Use of Adeno-Associated Virus as a Vector for Human Gene Therapy", Hum. Gene Ther., vol. 5, pp. 793-801, 1994.

Miller, "Human Gene Therapy Comes of Age", Nature, vol. 357, pp. 455-460, 1992.

Hartley, et al., "Naturally Occurring Murine Leukemia Viruses in Wild Mice: Characterization of a New 'Amphotropic' Class", J. Virol., vol. 19, No. 1, pp. 19-25, 1976.

Hosaka, et al., "Arg-X-Lys/Arg-Arg Motif as a Signal for Precursor Cleavage Catalyzed by Furin within the Constitutive Secretory Pathway", J. Biol. Chem., vol. 266, No. 19, pp. 12127-12130, 1991.

Ory, et al., "A Stable Human-Derived Packaging Cell Line for Production of High Titer Retrovirus/Vesicular Stomatitis Virus G Pseudotypes", Proc. Natl. Acad. Sci. USA, vol. 93, pp. 11400-11406, 1996.

Zufferey, et al., "Self-Inactivating Lentivirus Vector for Safe and Efficient In Vivo Gene Delivery", J. Virol., vol. 72, No. 12, pp. 9873-9880, 1998.

Ill, et al., "Optimization of the Human Factor VIII Complementary DNA Expression Plasmid for Gene Therapy of Hemophilia A", Blood Coagul. Fibrinolysis, vol. 8S2, pp. S23-S30, 1997.

Kim, et al., "Use of the Human Elongation Factor 1 α Promoter as a Versatile and Efficient Expression System", Gene, vol. 91, pp. 217-223, 1990.

Guo, et al., "Evaluation of Promoter Strength for Hepatic Gene Expression In Vivo Following Adenovirus-Mediated Gene Transfer", Gene Ther., vol. 3, pp. 802-810, 1996.

No, et al., "Ecdysone-Inducible Gene Expression in Mammalian Cells and Transgenic Mice", Proc. Natl. Acad. Sci. USA, vol. 93, pp. 3346-3351, 1996.

Suhr, et al., "High Level Transactivation by a Modified *Bombyx* Ecdysone Receptor in Mammalian Cells without Exogenous Retinoid X Receptor", Proc. Natl. Acad. Sci. USA, vol. 95, pp. 7999-8004, 1998.

Osterwalder, et al., "A Conditional Tissue-Specific Transgene Expression System Using Inducible GAL4", Proc. Natl. Acad. Sci., vol. 98, No. 22, pp. 12596-12601, 2001.

Knott, et al., "Tetracycline-Dependent Gene Regulation: Combinations of Transregulators Yield a Variety of Expression Windows", Biotechniques, vol. 32, No. 4, pp. 796, 798, 800, 2002.

Rivera, et al., "A Humanized System for Pharmacologic Control of Gene Expression", Nature Med., vol. 2, No. 9, pp. 1028-1032, 1996.

Ye, et al., "Regulated Delivery of Therapeutic Proteins After In Vivo Somatic Cell Gene Transfer", Science, vol. 283, pp. 88-91, 1999.

Capecchi, "High Efficiency Transformation by Direct Microinjection of DNA into Cultured Mammalian Cells", Cell, vol. 22, pp. 479-488, 1980.

Shigekawa, et al., "Electroporation of Eukaryotes and Prokaryotes: A General Approach to the Introduction of Macromolecules into Cells", Bio. Techn., vol. 6, No. 8, pp. 742-751, 1988.

Mannino et al., "Liposome Mediated Gene Transfer", Bio Techn., vol. 6, No. 7, pp. 682-690, 1988.

Felgner, et al., "Lipofection: A Highly Efficient, Lipid-Mediated DNA-Transfection Procedure", Proc. Natl. Acad. Sci. USA, vol. 84, pp. 7413-7417, 1987.

Klein, et al., "High-Velocity Microprojectiles for Delivering Nucleic Acids into Living Cells", Nature, vol. 327, pp. 70-73, 1987.

Jakobovits, et al., "Production and Selection of Antigen-Specific Fully Human Monoclonal Antibodies from Mice Engineered with Human Ig loci" Advanced Drug Delivery Reviews, vol. 31, pp. 33-42, 1998.

Mendez, et al., "Functional Transplant of Megabase Human Immunoglobin loci Recapitulates Human Antibody Response in Mice", Nature Genetics, vol. 15, pp. 146-156, 1997.

Jakobovits, et al., "Production of Fully Human Antibodies by Transgenic Mice", Current Opinion in Biotechnology, vol. 6, No. 5, pp. 561-566, 1995.

Green, et al., "Antigen-Specific Human Monoclonal Antibodies from Mice Engineered with Human Ig Heavy and Light Chain YACs", Nature Genetics, vol. 7, No. 1, pp. 13-21, 1994.

Pollock, et al., "Transgenic Milk as a Method for the Production of Recombinant Antibodies", Journal of Immunological Methods, vol. 231, pp. 147-157, 1999.

Young, et al., "Production of Recombinant Antibodies in the Milk of Transgenic Animals", Res. Immunol., Jul.-Aug., vol. 149, No. 6, pp. 609-610, 1998.

Houdebine, "Antibody Manufacture in Transgenic Animals and Comparisons with Other Systems", Opin. Biotechnology, vol. 13, pp. 625-629, 2002.

Little, et al., "Of Mice and Men: Hybridoma and Recombinant Antibodies", Immunol. Today, vol. 21, No. 8, pp. 364-370, 2000.

Gura, "Magic Bullets Hit the Target", Nature, vol. 417, pp. 584-586, 2002.

Streatfield, et al., "Plant-Based Vaccines", Int. J. Parasitol., vol. 33, Nos. 5-6, pp. 479-493, 2003.

Schillberg, et al., "Molecular Farming of Recombinant Antibodies in Plants", Cell Mol. Life Sci., vol. 60, No. 3, pp. 433-435, 2003.

Pogue, et al., "Making an Ally from an Enemy: Plant Virology and the New Agriculture", Ann. Rev. Phytopathol., vol. 40, pp. 45-74, 2002.

McCormick, et al., "Individualized Human scFv Vaccines Produced in Plants: Humoral Anti-Idiotype Responses in Vaccinated Mice Confirm Relevance to the Tumor Ig", J. Immun. Methods, vol. 278, Nos. 1-2, pp. 95-104, 2003.

Ghosh, et al., "Baculovirus as Mammalian Cell Expression Vector for Gene Therapy: An Emerging Strategy", Mol. Ther., vol. 6, No. 1, pp. 5-11, 2002.

Ikonomou, et al., "Insect Cell Culture for Industrial Production of Recombinant Proteins", Appl. Microbiol. Biotechnol., vol. 62, No. 1, pp. 1-20, 2003.

Zhang, et al., "High Levels of Foreign Gene Expression in Hepatocytes after Tail Vein Injections of Naked Plasmid DNA", Human Gene Ther., vol. 10, pp. 1735-1737, 1999.

Liu, et al., "Hydrodynamics-Based Transfection in Animals by Systemic Administration of Plasmid DNA", Gene Ther., vol. 6, pp. 1258-1266, 1999.

Takahashi, et al., "A Mutation of Furin Causes the Lack of Precursor-Processing Activity in Human Colon Carcinoma LoVo Cells", Biochem. Biophys. Res. Commun., vol. 195, pp. 1019-1026, 1993.

Ryan, et al., "Foot-and-Mouth Disease Virus 2A Oligopeptide Mediated Cleavage of an Artificial Polyprotein", EMBO J., vol. 13, No. 4, pp. 928-933, 1994.

De Felipe, et al., "Tricistronic and Tetracistronic Retroviral Vectors for Gene Transfer", Human Gene Ther., vol. 11, pp. 1921-1931, 2000.

Donnelly, et al., "Analysis of the Aphthovirus 2A/2B Polyprotein 'Cleavage' Mechanism Indicates not a Proteolytic Reaction, but a Novel Translational Effect: a Putative Ribosomal 'Skip'", J. Gen. Virol., vol. 82, pp. 1013-1025, 2001.

Ryan, et al., Specificity of Enzyme-Substrate Interactions in Foot-and-Mouth Disease Virus Polyprotein Processing, Virology, vol. 173, pp. 35-45, 1989.

Halpin, et al., "Self-Processing 2A-Polyproteins—A System for Coordinate Expression of Multiple Proteins in Transgenic Plants", The Plant Journal, vol. 17, No. 4, pp. 453-459, 1999.

Donnelly, et al., "The Cleavage Activities of Apthovirus and Cardiovirus 2A Proteins", J. Gen. Virol., vol. 78, pp. 13-21, 1997.

Roosien, et al., "Synthesis of Foot-and-Mouth Disease Virus Capsid Proteins in Insect Cells Using Baculovirus Expression Vectors", J. Gen. Virol., vol. 71, pp. 1703-1711, 1990.

Chaplin, et al., "Production of Interleukin-12 as a Self-Processing 2A Polypeptide", J. Interferon Cytokine Res., vol. 19, pp. 235-241, 1999.

De Felipe, et al., "Use of the 2A Sequence from Foot-and-Mouth Disease Virus in the Generation of Retroviral Vectors for Gene Therapy", Gene Ther., vol. 6, pp. 198-208, 1999.

Furler, et al., "Recombinant AAV Vectors Containing the Foot-and-Mouth Disease Virus 2A Sequence Confer Efficient Bicistronic Gene Expression in Cultured Cells and Rat Substantia Nigra Neurons", Gene Ther., vol. 8, pp. 864-873, 2001.

Ryan, et al., "Cleavage of Foot-and-Mouth Disease Virus Polyprotein is Mediated by Residues Located within a 19 Amino Acid Sequence", J. Gen. Virol., vol. 72, pp. 2727-2732, 1991.

Vakharia, et al., "Proteolytic Processing of Foot-and-Mouth Disease Virus Polyproteins Expressed in a Cell-Free System from Clone-Derived Transcripts", J. Gen. Virol., vol. 61, No. 10, pp. 3199-3207, 1987.

Burton, et al., "Coexpression of Factor VIII Heavy and Light Chain Adeno-Associated Viral Vectors Produces Biologically Active Protein", PNAS, vol. 96, No. 22, pp. 12725-12730, 1999.

Burton et al., Coexpression of factor VIII heavy and light chain adeno-associated viral vectors produces biologically active protein, *Proc. Natl. Acad. Sci. USA*, Oct. 1999, vol. 96, No. 22, pp. 12725-12730.

Noel et al., High In Vivo Production of a Model Monoclonal Antibody on Adenoviral Gene Transfer, *Human Gene Therapy*, Aug. 2002, vol. 13, pp. 1483-1493.

Fang, et al., 2005, "Stable Antibody Expression At Therapeutic Levels Using The 2A Peptide," Nature Biotechnology, 23(5): 584-590.

Gaken et al., 2000, "Fusagene Vectors: A Novel Strategy For The Expression of Multiple Genes From A Single Cistron," Gene Therapy 7:1979-1985.

Mah, et al., 2003, "Dual Vectors Expressing Murine Factor VIII Result In Sustained Correction Of Hemophilia A Mice," Human Gene Therapy 14:143-152.

Collet et al., A binary plasmid system for shuffling combinatorial antibody libraries, Proc. Natl. Acad. Sci. USA 89:10026-10030 (1992).

Loiler et al., Targeting recombinant adeno-associated virus vectors to enhance gene transfer to pancreatic islets and liver, Gene Therapy 10:1551-1558 (2003).

Altschul, 1997, Gapped BLAST and PSI-BLAST: a new generation of protein database search programs, Nucl Acid Res. 25(17):3389-3402.

Brinkhous et al., 2002, Preclinical pharmacology of albumin-free B-domain deleted recombinant factor VIII, Semin Thromb Hemos 28(3):269-72 (Abstract Only).

Chazenbalk et al., 1996, Evidence for negative cooperativity among human thyrotropin receptors overexpressed in mammalian cells, Endocrinology 137:4586-4591.

Eriksson et al., 2001, The manufacturing process for B-domain deleted recombinant factor VIII, Semin. Hematol. 38:24-31 (Abstract).

Gengrinovitch et al., 1995, Platelet factor-4 inhibits the mitogenic activity of VEGF121 and VEGF165 using several concurrent mechanisms, J. Biol. Chem. 270:15059-15065.

Green, 1999, Antibody engineering via genetic engineering of the mouse: XenoMouse strains are a vehicle for the facile generation of therapeutic human monoclonal antibodies, J. Immunol. Meth. 231:11-23.

Hagedorn, 2002, Domain swapping in a COOH-terminal fragment of platelet factor 4 generates potent angiogenesis inhibitors, Cancer Res. 62:6884-6890.

Hamstra and Rehemtulla, 1999, Toward an enzyme/prodrug strategy for cancer gene therapy: endogenous activation of carboxypeptidase A mutants by the PACE/Furin family of propeptidases, Hum. Gene Ther. 10:235-248.

High, 2003, Gene transfer as an approach to treating hemophilia, Semin. Thromb. Hemost. 29(1):107-20.

Holash et al., 2002, VEGF-Trap: a VEGF blocker with potent antitumor effects, Proc. Natl. Acad. Sci. USA 99(17):11393-98.

Kjalke et al., 1995, Amino acid residues 721-729 are required for full factor VIII activity, Eur. J. Biochem. 234(3):773-779.

Kolber et al., 1995, Inhibition of development of murine melanoma lung metastases by systemic administration of recombinant platelet factor 4, J. Natl. Cancer Instit.87:304-309.

Lamikarna et al., 2005, In vivo evaluation of an EIAV vector for the systemic genetic delivery of therapeutic antibodies, Gene Therapy 12:988-998.

Lenting et al., 1998, The life cycle of coagulation factor VIII in view of its structure and function, Blood 92(11):3983-3996.

Lind et al., 1995, Novel forms of B-domain deleted recombinant factor VIII molecules. Construction and biochemical charaterization, Eur. J. Biochem. 232:19-27.

Maione et al., 1990, Inhibition of angiogenesis by recombinant human platelet factor-4 and related peptides, Science 247:77-79.

Nakai et al., 1998, Adeno-associated viral vector-mediated gene transfer of human blood coagulation factor IX into mouse liver, Blood 91(12):4600-4607.

Niwa et al., 1991, Efficient selection for high-expression transfectants with a novel eukaryotic vector, Gene 108(2):193-199.

O'Rourke et al., 2002, Comparison of gene transfer efficiencies and gene expression levels achieved with equine infectious anemia virus- and human immunodeficiency virus type 1-derived lentivirus vectors, J. Virol. 76(3):1510-1515.

Osterberg et al., 2001, B-domain deleted recombinant factor VIII formulation and stability, Semin Hematol. 38(2 Suppl 4):40-3.

Perollet, 1998, Platelet factor 4 modulates fibroblast growth factor 2 (FGF-2) activity and inhibits FGF-2 dimerization, Blood 91:3289-32-99.

Pittman et al., 1993, Biochemical, immunological, and in vivo functional characterization of B-domain-deleted factor VIII, Blood 81:2925-2935.

Sandberg et al., 2001, Structural and functional characterization of B-domain deleted recombinant factor VIII, Semin. Hematol. 38(2 Suppl 4):4-12.

Sharpe et al., 1990, Growth inhibition of murine melanoma and human colon carcinoma by recombinant human platelet factor 4, J. Natl. Cancer Inst. 82:848-853.

Tanaka et al., 1997, Viral vector-mediated transduction of a modified platelet factor 4 cDNA inhibits angiogenesis and tumor growth,Nat. Med. 3(4):437-442.

Thompson, 2003, Structure and function of the factor VIII gene and protein, Semin. Thromb. Hemost. 29(1):11-22.

Vandendriessche et al., 2003, Gene therapy for the hemophilias, J. Thromb. Haemost. 1:1550.

Witte et al., 1998, Monoclonal antibodies targeting the VEGF receptor-2 (Flk1/KDR) as an anti-angiogenic therapeutic strategy, Cancer Metastasis 17:155-161.

Xu et al., 2001, Optimization of transcriptional regulatory elements for constructing plasmid vectors, Gene 272:149.

Yonemura et al., Efficient production of recombinant human factor VIII by co-expression of the heavy and light chains, Protein Eng. 6:669-674.

Li et al., A hepatocellular carcinoma-specific adenovirus variant, CV890, eliminates distant human liver tumors in combination with doxorubicin, Cancer Res. 61:6428-6436 (2001).

National Center for Biotechnology Information (http://www.ncbi.nlm.nih.gov/), p. 1-2, downloaded Nov. 19, 2004.

* cited by examiner

SEQUENCE LISTING

<160> NUMBER OF SEQ ID NOS: 15

<210> SEQ ID NO 1
<211> LENGTH: 19
<212> TYPE: PRT

```
<213> ORGANISM: Artificial Sequence
<220> FEATURE:
<223> OTHER INFORMATION: FMDV 2A domain

<400> SEQUENCE: 1

Leu Leu As

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 7
<211> LENGTH: 58
<212> TYPE: PRT
<213> ORGANISM: Artificial Sequence
<220> FEATURE:
<223> OTHER INFORMATION: FMDV 2A domain

<400> SEQUENCE: 7

Val Thr Glu Leu Leu Tyr Arg Met Lys Arg Ala Glu Thr Tyr Cys Pro
1               5                   10                  15

Arg Pro Leu Leu Ala Ile His Pro Thr Glu Ala Arg His Lys Gln Lys
            20                  25                  30

Ile Val Ala Pro Val Lys Gln Thr Leu Asn Phe Asp Leu Leu Lys Leu
        35                  40                  45

Ala Gly Asp Val Glu Ser Asn Pro Gly Pro
    50                  55

<210> SEQ ID NO 8
<211> LENGTH: 40
<212> TYPE: PRT
<213> ORGANISM: Artificial Sequence
<220> FEATURE:
<223> OTHER INFORMATION: FMDV 2A domain

<400> SEQUENCE: 8

Leu Leu Ala Ile His Pro Thr Glu Ala Arg His Lys Gln Lys Ile Val
1               5                   10                  15

Ala Pro Val Lys Gln Thr Leu Asn Phe Asp Leu Leu Lys Leu Ala Gly
            20                  25                  30

Asp Val Glu Ser Asn Pro Gly Pro
        35                  40

<210> SEQ ID NO 9
<211> LENGTH: 33
<212> TYPE: PRT
<213> ORGANISM: Artificial Sequence
<220> FEATURE:
<223> OTHER INFORMATION: FMDV 2A domain

<400> SEQUENCE: 9

Glu Ala Arg His Lys Gln Lys Ile Val Ala Pro Val Lys Gln Thr Leu
1               5                   10                  15

Asn Phe Asp Leu Leu Lys Leu Ala Gly Asp Val Glu Ser Asn Pro Gly
            20                  25                  30

Pro

<210> SEQ ID NO 10
<211> LENGTH: 5
<212> TYPE: PRT
<213> ORGANISM: Artificial Sequence
<220> FEATURE:
<223> OTHER INFORMATION: consensus sequence of furin cleavage site
<220> FEATURE:
<221> NAME/KEY: VARIANT
<222> LOCATION: 2
<223> OTHER INFORMATION: Xaa = Any Amino Acid

<400> SEQUENCE: 10

```
Arg Xaa Lys Arg Arg
1               5

<210> SEQ ID NO 11
<211> LENGTH: 5
<212> TYPE: PRT
<213> ORGANISM: Artificial Sequence
<220> FEATURE:
<223> OTHER INFORMATION: Factor Xa cleavage site sequence

<400> SEQUENCE: 11

Ile Glu Asp Gly Arg
1               5

<210> SEQ ID NO 12
<211> LENGTH: 10
<212> TYPE: PRT
<213> ORGANISM: Artificial Sequence
<220> FEATURE:
<223> OTHER INFORMATION: Signal peptidase I cleavage site sequence

<400> SEQUENCE: 12

Leu Ala Gly Phe Ala Thr Val Ala Gln Ala
1               5                   10

<210> SEQ ID NO 13
<211> LENGTH: 6
<212> TYPE: PRT
<213> ORGANISM: Artificial Sequence
<220> FEATURE:
<223> OTHER INFORMATION: Thrombin cleavage site sequence

<400> SEQUENCE: 13

Leu Val Pro Arg Gly Ser
1               5

<210> SEQ ID NO 14
<211> LENGTH: 10
<212> TYPE: PRT
<213> ORGANISM: Artificial Sequence
<220> FEATURE:
<223> OTHER INFORMATION: HF2AL construct C-terminal sequence

<400> SEQUENCE: 14

Ser Leu Ser His Ser Pro Gly Lys Arg Ala
1               5                   10

<210> SEQ ID NO 15
<211> LENGTH: 4
<212> TYPE: PRT
<213> ORGANISM: Artificial Sequence
<220> FEATURE:
<223> OTHER INFORMATION: furin cleavage site sequence

<400> SEQUENCE: 15

Arg Ala Lys Arg
1
```

COMPOSITIONS AND METHODS FOR ENHANCED EXPRESSION OF IMMUNOGLOBULINS FROM A SINGLE VECTOR USING A PEPTIDE CLEAVAGE SITE

CROSS-REFERENCE TO RELATED APPLICATIONS

This application is a continuation-in-part of U.S. patent application Ser. No. 10/452,253, filed Jun. 3, 2003 and claims the priority benefit of U.S. Provisional Patent Application No. 60/540,554, filed Feb. 2, 2004. The priority applications are hereby incorporated by reference herein in their entirety.

FIELD OF THE INVENTION

The invention relates to novel vector or plasmid constructs designed to express self-processing recombinant full length immunoglobulins or fragments thereof. The constructs may be used for ex vivo or in vivo delivery or expression of heterologous immunoglobulin coding sequences to a cell or organ, or in vitro for the production of recombinant immunoglobulins by vector-transfected cells.

BACKGROUND OF THE INVENTION

The use of antibodies as diagnostic tools and therapeutic modalities has found increasing use in recent years. The first FDA-approved monoclonal antibody, Rituxan® (Rituximab) was approved in 1997 for the treatment of patients with non-Hodgkin's lymphoma and soon thereafter 1998, Herceptin®, a humanized monoclonal antibody for treatment of patients with metastatic breast cancer was also approved. Numerous antibody-based therapies are showing promise in various stages of clinical development. One limitation in widespread clinical application of antibody technology is that typically large amounts of antibody are required for therapeutic efficacy and the costs associated with sufficient production are significant. Chinese Hamster Ovarian (CHO) cells and NSO2 myeloma cells are the most commonly used mammalian cell lines for commercial scale production of glycosylated human proteins like antibodies. Mammalian cell line production yields typically range from 50-250 mg/L for 5-7 day culture in a batch fermentor or 300-600 mg/L in 7-12 days in fed batch fermentors. Non-glycosylated proteins can be successfully produced in yeast (e.g., insulin production by Novo Nordisk) or E. Coli (e.g., insulin production by Eli Lilly, and Fab production by Celltech).

Previous attempts to express a full length antibody/immunoglobulin molecule via recombinant DNA technology using a single vector have met with limited success, typically resulting in unequal levels of expression of the heavy and light chains of the antibody/immunoglobulin molecule, and more particularly, a lower level of expression for the second gene. The unequal expression of heavy and light chains within the cell results in an overall low yield of full length antibody. In order to express high levels of a fully biological functional antibody from a single vector, equimolar expression of the heavy and light chains is required. Additionally, conventional vectors relying on dual promoter regulation of gene expression are invariably affected by promoter interaction (i.e., promoter interference) which may compromise equimolar expression of the genes. Other factors that limit the ability to express two or more coding sequences from a single vector include the packaging limitation of the vector itself. For example, in considering the appropriate vector/coding sequence, factors to be considered include: packaging capacity of the vector (e.g., approx. 4,500 bp for AAV), which can limit the size of expressible coding sequences; the duration of in vitro/in vivo expression of the recombinant protein by a vector-transfected cell or organ (e.g., short term expression for adenoviral vectors); the cell types infected by the vector if a viral vector is used; and the desired expression level of the gene product(s) which is generated. The requirement for controlled expression of two or more gene products together with the packaging limitations of viral vectors such as adenovirus and AAV, limits the choices with respect to vector construction and systems for expression of immunoglobulins or fragments thereof.

In order to express two or more protein or polypeptide sequences from a single vector, two or more promoters or an internal ribosome entry site (IRES) sequence are used to drive expression of individual genes. The use of two promoters within a single vector can result in low protein expression due to promoter interference. When two genes are linked with an IRES sequence, the expression level of the second gene is often significantly weaker than the first gene (Furler et al., Gene Therapy 8:864-873, 2001).

The linking of proteins in the form of polyproteins in a single open reading frame is a strategy adopted in the replication of many viruses including picomaviridae. Upon translation, virus-encoded proteinases mediate rapid intramolecular (cis) cleavage of a polyprotein to yield discrete mature protein products. Foot and Mouth Disease viruses (FMDV) are a group within the picomaviridae which express a single, long open reading frame encoding a polyprotein of approximately 225 kD. The full length translation product undergoes rapid intramolecular (cis) cleavage at the C-terminus of a 2A region occurring between the capsid protein precursor (P1-2A) and replicative domains of the polyprotein 2BC and P3, and this cleavage is mediated by proteinase-like activity of the 2A region itself (Ryan et al., J. Gen. Virol. 72:2727-2732, 1991); Vakharia et al., J. Virol. 61:3199-3207, 1987). Ryan designed constructs identifying the essential amino acid residues for expression of the cleavage activity by the FMDV 2A region. 2A domains have also been characterized from aphthoviridea and cardioviridae of the picomavirus family (Donnelly et al., J. Gen. Virol. 78:13-21, 1997).

There remains a need for improved gene expression systems for expression of full length immunoglobulins and fragments thereof which provide advantages relative to currently available technology (i.e., the use of an IRES or two or more promoters).

The present invention addresses this need by demonstrating the feasibility and use of a single vector construct which encodes a self-processing peptide for expression of a biologically functional polypeptide, such as an immunoglobulin or fragment thereof.

SUMMARY OF THE INVENTION

The present invention provides a system for expression of a full length immunoglobulin or fragment thereof based on essentially equal expression of heavy and light chain coding sequences under the transcriptional control of a single promoter, wherein translation is mediated by self-processing cleavage site, e.g., a 2A or 2A-like sequence.

In one aspect, the invention provides a vector for expression of a recombinant immunoglobulin, which includes a promoter operably linked to the coding sequence for a first chain of an immunoglobulin molecule or a fragment thereof, a sequence encoding a self-processing cleavage site and the coding sequence for a second chain of an immunoglobulin molecule or fragment thereof, wherein the sequence encoding the self-processing cleavage site is inserted between the coding sequence for the first chain of the immunoglobulin molecule and the coding sequence for the second chain of the immunoglobulin molecule. Either the first or second chain of the immunoglobulin molecule may be a heavy chain or a light chain and the sequence encoding the recombinant immunoglobulin may be a full length coding sequence or a fragment thereof.

The vector may be any recombinant vector capable of expression of a full length immunoglobulin molecule or fragment thereof, for example, an adeno-associated virus (AAV) vector, a lentivirus vector, a retrovirus vector, a replication competent adenovirus vector, a replication deficient adenovirus vector and a gutless adenovirus vector, a herpes virus vector or a nonviral vector (plasmid).

Preferred self-processing cleavage sites include a 2A sequence, e.g., a 2A sequence derived from Foot and Mouth Disease Virus (FMDV).

In a further preferred aspect, the vector comprises a sequence which encodes an additional proteolytic cleavage site located between the coding sequence for the first chain of the immunoglobulin molecule or fragment thereof and the coding sequence for the second chain of the immunoglobulin molecule or fragment thereof (i.e., adjacent the sequence for a self-processing cleavage site, such as a 2A cleavage site). In one exemplary approach, the additional proteolytic cleavage site is a furin cleavage site with the consensus sequence RXK(R)R (SEQ ID NO: 10).

A vector for recombinant immunoglobulin expression using a self-processing peptide may include any of a number of promoters, wherein the promoter is constitutive, regulatable or inducible, cell type specific, tissue-specific, or species specific.

The vector may further comprise a signal sequence for the coding sequences.

In a preferred aspect of the invention, heavy and light chain immunoglobulin (antibody) coding sequences are expressed in an equimolar or close to an equimolar ratio.

The invention further provides host cells or stable clones of host cells infected with a vector that comprises: (i) a sequence encoding heavy and light chains of an immunoglobulin (i.e., an antibody); (ii) a sequence encoding a self-processing cleavage site; and may further comprise (iii) a sequence encoding an additional proteolytic cleavage site. Use of such cells or clones in generating full length recombinant immunoglobulins or fragments thereof is also included within the scope of the invention.

In a related aspect, the invention provides a recombinant immunoglobulin molecule or fragment thereof produced by such a cell or clones, wherein the immunoglobulin comprises amino acids derived from a self processing cleavage site, and methods for producing the same.

Other aspects, features and advantages of the invention are apparent from the following description of the invention, provided for the purpose of disclosure when taken in conjunction with the accompanying drawings.

BRIEF DESCRIPTION OF THE DRAWINGS

FIGS. 6A and B show the results of Western blot analysis of rat ant-FLK-1 antibody (IgG) in 293T cell supernatants following transfection of an anti-FLK-1 Ig/AAV H2AL plasmid. FIG. 6A shows the results of PAGE using a 12% native gel and FIG. 6B shows the results of PAGE using a 12% reducing gel wherein Lane 1 shows IgG produced from a hybridoma; Lane 2 shows IgG expressed using a 2A sequence in 293T cells and Lane 3 is a 293T mock control.

DETAILED DESCRIPTION OF THE INVENTION

Figure 1:
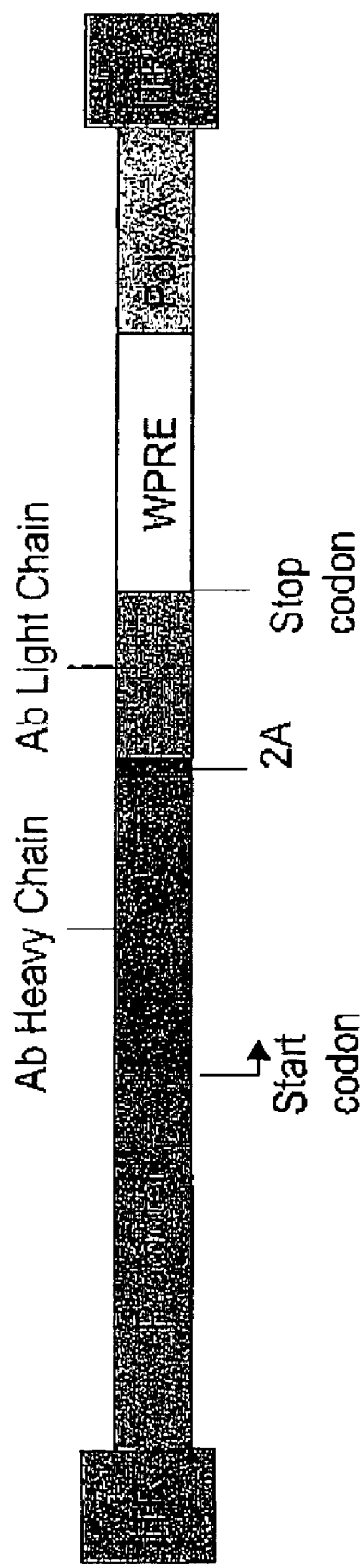
FIG. 1 depicts an AAV expression cassette encoding the heavy and light chain for an antibody as described in Example 1.
Figure 2:
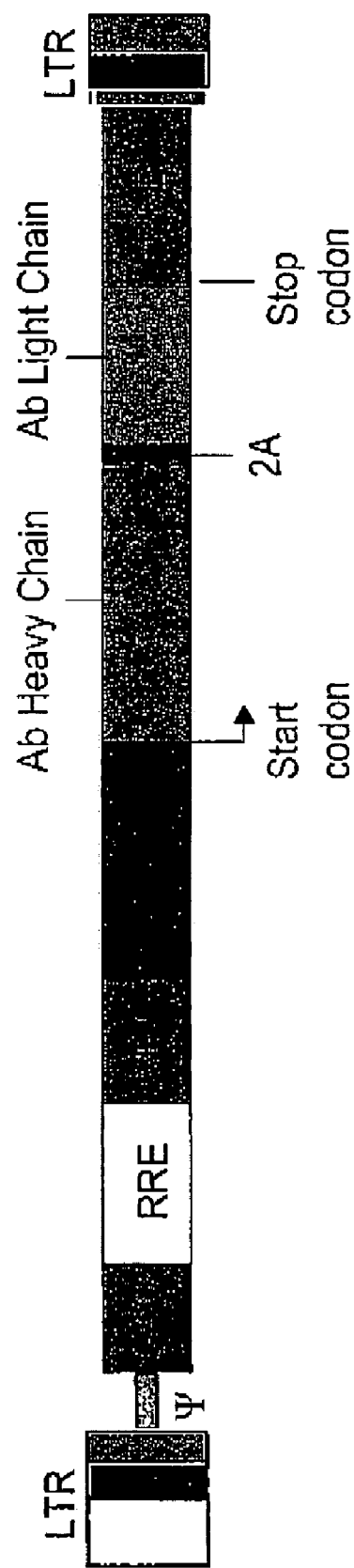
FIG. 2 depicts a lentiviral expression cassette encoding the heavy and light chain for an antibody.
Figure 3:
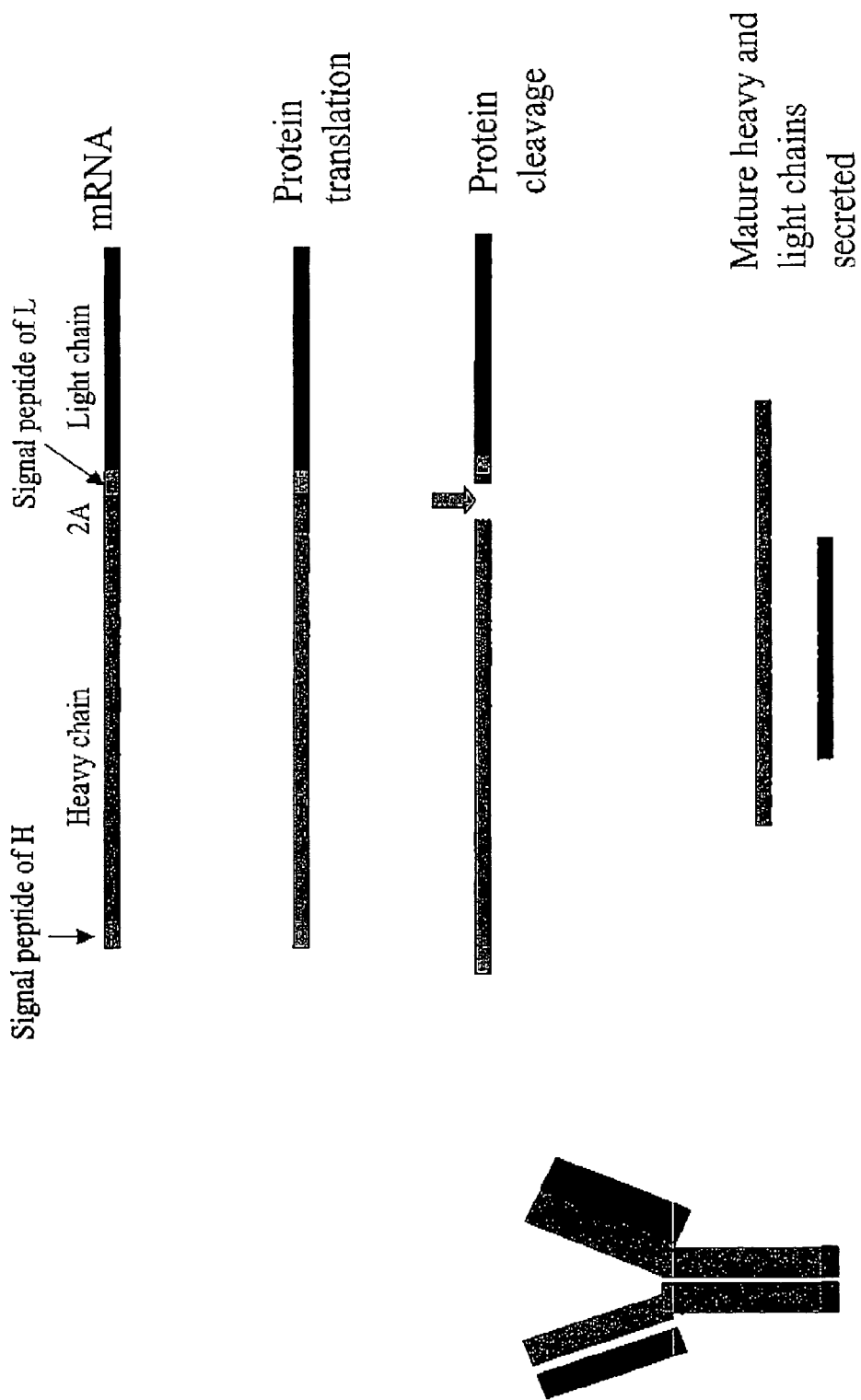
FIG. 3 is a schematic illustration of an example of the bioprocessing of a polyprotein resulting in generation of a full length antibody (immunoglobulin) using an H2AL (heavy chain—2A sequence—light chain) construct.

The present invention provides single vector constructs for expression of an immunoglobulin molecule or fragment thereof and methods for in vitro or in vivo use of the same. The vectors have a self-processing cleavage sequence between a first and second immunoglobulin coding sequence allowing for expression of a functional antibody molecule using a single promoter. Exemplary vector constructs comprise a sequence encoding a self-processing cleavage site between open reading frames and may further comprise an additional proteolytic cleavage site adjacent to the self-processing cleavage site for removal of amino acids that comprise the self-processing cleavage site following cleavage. The vector constructs find utility in methods relating to enhanced production of full length biologically active immunoglobulins or fragments thereof in vitro and in vivo.

The various compositions and methods of the invention are described below. Although particular compositions and methods are exemplified herein, it is understood that any of a number of alternative compositions and methods are applicable and suitable for use in practicing the invention. It will also be understood that an evaluation of the immunoglobulin expression constructs (vectors) and methods of the invention may be carried out using procedures standard in the art. The practice of the present invention will employ, unless otherwise indicated, conventional techniques of cell biology, molecular biology (including recombinant techniques), microbiology, biochemistry and immunology, which are within the scope of those of skill in the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991), each of which is expressly incorporated by reference herein.

Definitions

Unless otherwise indicated, all terms used herein have the same meaning as they would to one skilled in the art and the practice of the present invention will employ, conventional techniques of microbiology and recombinant DNA technology, which are within the knowledge of those of skill of the art.

The term "vector", as used herein, refers to a DNA or RNA molecule such as a plasmid, virus or other vehicle, which contains one or more heterologous or recombinant DNA sequences and is designed for transfer between different host cells. The terms "expression vector" and "gene therapy vector" refer to any vector that is effective to incorporate and express heterologous DNA fragments in a cell. A cloning or expression vector may comprise additional elements, for example, the expression vector may have two replication systems, thus allowing it to be maintained in two organisms, for example in human cells for expression and in a prokaryotic host for cloning and amplification. Any suitable vector can be employed that is effective for introduction of nucleic acids into cells such that protein or polypeptde expression results, e.g. a viral vector or non-viral plasmid vector. Any cells effective for expression, e.g., insect cells and eukaryofic cells such as yeast or mammalian cells are useful in practicing the invention.

The terms "heterologous DNA" and "heterologous RNA" refer to nucleotides that are not endogenous (native) to the cell or part of the genome in which they are present. Generally heterologous DNA or RNA is added to a cell by transduction, infection, transfection, transformation or the like, as further described below. Such nucleotides generally include at least one coding sequence, but the coding sequence need not be expressed. The term "heterologous DNA" may refer to a "heterologous coding sequence" or a "transgene".

As used herein, the terms "protein" and "polypeptide" may be used interchangeably and typically refer to "proteins" and "polypeptides" of interest that are expresses using the self processing cleavage site-containing vectors of the present invention. Such "proteins" and "polypeptides" may be any protein or polypeptide useful for research, diagnostic or therapeutic purposes, as further described below.

The term "replication defective" as used herein relative to a viral gene therapy vector of the invention means the viral vector cannot independently further replicate and package its genome. For example, when a cell of a subject is infected with rAAV virions, the heterologous gene is expressed in the infected cells, however, due to the fact that the infected cells lack AAV rep and cap genes and accessory function genes, the rAAV is not able to replicate.

As used herein, a "retroviral transfer vector" refers to an expression vector that comprises a nucleotide sequence that encodes a transgene and further comprises nucleotide sequences necessary for packaging of the vector. Preferably, the retroviral transfer vector also comprises the necessary sequences for expressing the transgene in cells.

As used herein, "packaging system" refers to a set of viral constructs comprising genes that encode viral proteins involved in packaging a recombinant virus. Typically, the constructs of the packaging system will ultimately be incorporated into a packaging cell.

As used herein, a "second generation" lentiviral vector system refers to a lentiviral packaging system that lacks functional accessory genes, such as one from which the accessory genes, vif, vpr, vpu and nef, have been deleted or inactivated. See, e.g., Zufferey et al., 1997, Nat. Biotechnol. 15:871-875.

As used herein, a "third generation" lentiviral vector system refers to a lentiviral packaging system that has the characteristics of a second generation vector system, and further lacks a functional tat gene, such as one from which the tat gene has been deleted or inactivated. Typically, the gene encoding rev is provided on a separate expression construct. See, e.g., Dull et al., 1998, J. Virol. 72(11):8463-8471.

As used herein, "pseudotyped" refers to the replacement of a native envelope protein with a heterologous or functionally modified envelope protein.

The term "operably linked" as used herein relative to a recombinant DNA construct or vector means nucleotide components of the recombinant DNA construct or vector are functionally related to one another for operative control of a selected coding sequence. Generally, "operably linked" DNA sequences are contiguous, and, in the case of a secretory leader, contiguous and in reading frame. However, enhancers do not have to be contiguous.

As used herein, the term "gene" or "coding sequence" means the nucleic acid sequence which is transcribed (DNA) and translated (mRNA) into a polypeptide in vitro or in vivo when operably linked to appropriate regulatory sequences. The gene may or may not include regions preceding and following the coding region, e.g. 5' untranslated (5' UTR) or "leader" sequences and 3' UTR or "trailer" sequences, as well as intervening sequences (introns) between individual coding segments (exons).

A "promoter" is a DNA sequence that directs the binding of RNA polymerase and thereby promotes RNA synthesis, i.e., a minimal sequence sufficient to direct transcription. Promoters and corresponding protein or polypeptide expression may be cell-type specific, tissue-specific, or species specific. Also included in the nucleic acid constructs or vectors of the invention are enhancer sequences which may or may not be contiguous with the promoter sequence. Enhancer sequences influence promoter-dependent gene expression and may be located in the 5' or 3' regions of the native gene.

"Enhancers" are cis-acting elements that stimulate or inhibit transcription of adjacent genes. An enhancer that inhibits transcription also is termed a "silencer". Enhancers can function (i.e., can be associated with a coding sequence)

in either orientation, over distances of up to several kilobase pairs (kb) from the coding sequence and from a position downstream of a transcribed region.

A "regulatable promoter" is any promoter whose activity is affected by a cis or trans acting factor (e.g., an inducible promoter, such as an external signal or agent).

A "constitutive promoter" is any promoter that directs RNA production in many or all tissue/cell types at most times, e.g., the human CMV immediate early enhancer/promoter region which promotes constitutive expression of cloned DNA inserts in mammalian cells.

The terms "transcriptional regulatory protein", "transcriptional regulatory factor" and "transcription factor" are used interchangeably herein, and refer to a nuclear protein that binds a DNA response element and thereby transcriptionally regulates the expression of an associated gene or genes. Transcriptional regulatory proteins generally bind directly to a DNA response element, however in some cases binding to DNA may be indirect by way of binding to another protein that in turn binds to, or is bound to a DNA response element.

As used herein, an "internal ribosome entry site" or "IRES" refers to an element that promotes direct internal ribosome entry to the initiation codon, such as ATG, of a cistron (a protein encoding region), thereby leading to the cap-independent translation of the gene. See, e.g., Jackson R J, Howell M T, Kaminski A (1990) Trends Biochem Sci 15(12):477-83) and Jackson R J and Kaminski, A. (1995) RNA 1(10):985-1000. The examples described herein are relevant to the use of any IRES element, which is able to promote direct internal ribosome entry to the initiation codon of a cistron. "Under translational control of an IRES" as used herein means that translation is associated with the IRES and proceeds in a cap-independent manner.

A "self-processing cleavage site" or "self-processing cleavage sequence" is defined herein as a post-translational or co-translational processing cleavage site sequence. Such a "self-processing cleavage" site or sequence refers to a DNA or amino acid sequence, exemplified herein by a 2A site, sequence or domain or a 2A-like site, sequence or domain. As used herein, a "self-processing peptide" is defined herein as the peptide expression product of the DNA sequence that encodes a self-processing cleavage site or sequence, which upon translation, mediates rapid intramolecular (cis) cleavage of a protein or polypeptide comprising the self-processing cleavage site to yield discrete mature protein or polypeptide products.

As used herein, the term "additonal proteolytic cleavage site", refers to a sequence which is incorporated into an expression construct of the invention adjacent a self-processing cleavage site, such as a 2A or 2A like sequence, and provides a means to remove additional amino acids that remain following cleavage by the self processing cleavage sequence. Exemplary "additional proteolytic cleavage sites" are described herein and include, but are not limited to, furin cleavage sites with the consensus sequence RXK(R)R (SEQ ID NO: 10). Such furin cleavage sites can be cleaved by endogenous subtilisin-like proteases, such as furin and other serine proteases within the protein secretion pathway.

As used herein, the terms "immunoglobulin" and "antibody" refer to intact molecules as well as fragments thereof, such as Fa, F(ab')2, and Fv, which are capable of binding an antigenic determinant. Such an "immunoglobulin" and "antibody" is composed of two identical light polypeptide chains of molecular weight approximately 23,000 daltons, and two identical heavy chains of molecular weight 53,000-70,000. The four chains are joined by disulfide bonds in a "Y" configuration. Heavy chains are classified as gamma (IgG), mu(IgM), alpha (IgA), delta (IgD) or epsilon (IgE) and are the basis for the class designations of immunoglobulins, which determines the effector function of a given antibody. Light chains are classified as either kappa or lambda. When reference is made herein to an "immunoglobulin or fragment thereof", it will be understood that such a "fragment thereof" is an immunologically functional immunoglobulin fragment.

The term "humanized antibody" refers to an antibody molecule in which one or more amino acids have been replaced in the non-antigen binding regions in order to more closely resemble a human antibody, while still retaining the original binding activity of the antibody. See, e.g., U.S. Pat. No. 6,602,503.

The term "antigenic determinant", as used herein, refers to that fragment of a molecule (i.e., an epitope) that makes contact with a particular antibody. Numerous regions of a protein or fragment of a protein may induce the production of antibodies which bind specifically to a given region or three-dimensional structure on the protein. These regions or structures are referred to as antigenic determinants. An antigenic determinant may compete with the intact antigen (i.e., the immunogen used to elicit the immune response) for binding to an antibody.

The term "fragment," when referring to a recombinant protein or polypeptide of the invention means a polypeptide which has an amino acid sequence which is the same as part of, but not all of, the amino acid sequence of the corresponding full length protein or polypeptide, which retains at least one of the functions or activities of the corresponding full length protein or polypeptide. The fragment preferably includes at least 20-100 contiguous amino acid residues of the full length protein or polypeptide.

The terms "administering" or "introducing", as used herein refer to delivery of a vector for recombinant protein expression to a cell or to cells and or organs of a subject. Such administering or introducing may take place in vivo, in vitro or ex vivo. A vector for recombinant protein or polypeptide expression may be introduced into a cell by transfection, which typically means insertion of heterologous DNA into a cell by physical means (e.g., calcium phosphate transfection, electroporation, microinjection or lipofection); infection, which typically refers to introduction by way of an infectious agent, i.e. a virus; or transduction, which typically means stable infection of a cell with a virus or the transfer of genetic material from one microorganism to another by way of a viral agent (e.g., a bacteriophage).

"Transformation" is typically used to refer to bacteria comprising heterologous DNA or cells which express an oncogene and have therefore been converted into a continuous growth mode such as tumor cells. A vector used to "transform" a cell may be a plasmid, virus or other vehicle.

Typically, a cell is referred to as "transduced", "infected", "transfected" or "transformed" dependent on the means used for administration, introduction or insertion of heterologous DNA (i.e., the vector) into the cell. The terms "transduced", "transfected" and "transformed" may be used interchangeably herein regardless of the method of introduction of heterologous DNA.

As used herein, the terms "stably transformed", "stably transfected" and "transgenic" refer to cells that have a non-native (heterologous) nucleic acid sequence integrated into the genome. Stable transfection is demonstrated by the establishment of cell lines or clones comprised of a population of daughter cells containing the transfected DNA stably integrated into their genomes. In some cases, "transfection" is not stable, i.e., it is transient. In the case of transient transfection, the exogenous or heterologous DNA is expressed, however, the introduced sequence is not integrated into the genome and is considered to be episomal.

As used herein, "ex vivo administration" refers to a process where primary cells are taken from a subject, a vector is administered to the cells to produce transduced, infected or transfected recombinant cells and the recombinant cells are readministered to the same or a different subject.

A "multicistronic transcript" refers to an mRNA molecule that contains more than one protein coding region, or cistron. A mRNA comprising two coding regions is denoted a "bicistronic transcript." The "5'-proximal" coding region or cistron is the coding region whose translation initiation codon (usually AUG) is closest to the 5' end of a multicistronic mRNA molecule. A "5'-distal" coding region or cistron is one whose translation initiation codon (usually AUG) is not the closest initiation codon to the 5' end of the mRNA. The terms "5'-distal" and "downstream" are used synonymously to refer to coding regions that are not adjacent to the 5' end of a mRNA molecule.

As used herein, "co-transcribed" means that two (or more) coding regions or polynucleotides are under transcriptional control of a single transcriptional control or regulatory element.

The term "host cell", as used herein refers to a cell which has been transduced, infected, transfected or transformed with a vector. The vector may be a plasmid, a viral particle, a phage, etc. The culture conditions, such as temperature, pH and the like, are those previously used with the host cell selected for expression, and will be apparent to those skilled in the art. It will be appreciated that the term "host cell" refers to the original transduced, infected, transfected or transformed cell and progeny thereof.

As used herein, the terms "biological activity" and "biologically active", refer to the activity attributed to a particular protein in a cell line in culture or in a cell-free system, such as a ligand-receptor assay in ELISA plates. The "biological activity" of an "immunoglobulin", "antibody" or fragment thereof refers to the ability to bind an antigenic determinant and thereby facilitate immunological function.

As used herein, the terms "tumor" and "cancer" refer to a cell that exhibits a loss of growth control and forms unusually large clones of cells. Tumor or cancer cells generally have lost contact inhibition and may be invasive and/or have the ability to metastasize.

Immunoglobulins and Fragments Thereof

Antibodies are immunoblobulin proteins that are heterodimers of a heavy and light chain and have proven extremely difficult to express in a full length form from a single vector in mammalian culture expression systems. Three methods are currently used for production of vertebrate antibodies, in vivo immunizabon of animals to produce "polyclonal" antibodies, in vitro cell culture of B-cell hybridomas to produce monoclonal antibodies (Kohler, et al., Eur. J. Immunol., 6:511, 1976; Antibodies: A Laboratory Manual, Cold Spring Harbor Laboratory, 1988; incorporated by reference herein) and recombinant DNA technology (described for example in Cabilly et al., U.S. Pat. No. 6,331,415, incorporated by reference herein).

The basic molecular structure of immunoglobulin polypeptides is well known to include two identical light chains with a molecular weight of approximately 23,000 daltons, and two identical heavy chains with a molecular weight 53,000-70,000, where the four chains are joined by disulfide bonds in a "Y" configuration. The amino acid sequence runs from the N-terminal end at the top of the Y to the C-terminal end at the bottom of each chain. At the N-terminal end is a variable region (of approximately 100 amino acids in length) which provides for the specificity of antigen binding.

The present invention is directed to improved methods for production of immunoglobulins of all types, including, but not limited to full length antibodies and antibody fragments having a native sequence (i.e. that sequence produced in response to stimulation by an antigen), single chain antibodies which combine the antigen binding variable region of both the heavy and light chains in a single stably-folded polypeptide chain; univalent antibodies (which comprise a heavy chain/light chain dimer bound to the Fc region of a second heavy chain); "Fab fragments" which include the full "Y" region of the immunoglobulin molecule, i.e., the branches of the "Y", either the light chain or heavy chain alone, or portions, thereof (i.e., aggregates of one heavy and one light chain, commonly known as Fab'); "hybrid immunoglobulins" which have specificity for two or more different antigens (e.g., quadromas or bispecific antibodies as described for example in U.S. Pat. No. 6,623,940); "composite immunoglobulins" wherein the heavy and light chains mimic those from different species or specificities; and "chimeric antibodies" wherein portions of each of the amino acid sequences of the heavy and light chain are derived from more than one species (i.e., the variable region is derived from one source such as a murine antibody, while the constant region is derived from another, such as a human antibody).

The compositions and methods of the invention find utility in production of immunoglobulins or fragments thereof wherein the heavy or light chain is "mammalian", "chimeric" or modified in a manner to enhance its efficacy. Modified antibodies include both amino acid and nucleic acid sequence variants which retain the same biological activity of the unmodified form and those which are modified such that the activity is altered, i.e., changes in the constant region that improve complement fixation, interaction with membranes, and other effector functions, or changes in the variable region that improve antigen binding characteristics. The compositions and methods of the invention further include catalytic immunoglobulins or fragments thereof.

A "variant" immunoglobulin-encoding polynucleotide sequence may encode a "variant" immunoglobulin amino acid sequence which is altered by one or more amino acids from the reference polypeptide sequence. The variant polynucleotide sequence may encode a variant amino acid sequence which contains "conservative" substitutions, wherein the substituted amino acid has structural or chemical properties similar to the amino acid which it replaces. In addition, or alternatively, the variant polynucleotide sequence may encode a variant amino acid sequence which contains "non-conservative" substitutions, wherein the substituted amino acid has dissimilar structural or chemical properties to the amino acid which it replaces. Variant immunoglobulin-encoding polynucleotides may also encode variant amino acid sequences which contain amino acid insertions or deletions, or both. Furthermore, a variant "immunoglobulin-encoding polynucleotide may encode the same polypeptide as the reference polynucleotide sequence but, due to the degeneracy of the genetic code, has a polynucleotide sequence which is altered by one or more bases from the reference polynucleotide sequence.

The term "fragment," when referring to a recombinant immunoglobulin of the invention means a polypeptide which has an amino acid sequence which is the same as part of but not all of the amino acid sequence of the corresponding full length immunoglobulin protein, which either retains essentially the same biological function or activity as the corresponding full length protein, or retains at least one of the functions or activities of the corresponding full length protein. The fragment preferably includes at least 20-100 contiguous amino acid residues of the full length immunoglobulin.

The potential of antibodies as therapeutic modalities is currently limited by the production capacity and excessive cost of the current technology. An improved viral or non-viral single expression vector for immunoblobulin production would permit the expression and delivery of two or more coding sequences, i.e., immunoglobulins with bi- or multiple-specificities from a single vector. The present invention addresses these limitations and is applicable to any immunoglobulin (i.e. an antibody) or fragment thereof as further detailed herein, including engineered antibodies such as single chain antibodies, full-length antibodies or antibody fragments.

Internal Ribosome Entry Site (IRES)

IRES elements were first discovered in picornavirus mRNAs (Jackson R J, Howell M T, Kaminski A (1990) Trends Biochem Sci 15(12):477-83) and Jackson RJ and Kaminski, A. (1995) RNA 1(10):985-1000). Examples of IRES generally employed by those of skill in the art include those referenced in Table I, as well as those described in U.S. Pat. No. 6,692,736. Examples of "IRES" known in the art include, but are not limited to IRES obtainable from picornavirus (Jackson et al., 1990) and IRES obtainable from viral or cellular mRNA sources, such as for example, immunoglobulin heavy-chain binding protein (BiP), the vascular endothelial growth factor (VEGF) (Huez et al. (1998) Mol. Cell. Biol. 18(11):6178-6190), the fibroblast growth factor 2 (FGF-2), and insulin-like growth factor (IGFII), the translational initiation factor eIF4G and yeast transcription factors TFIID and HAP4, the encephelomycarditis virus (EMCV) which is commercially available from Novagen (Duke et al. (1992) J. Virol 66(3):1602-9) and the VEGF IRES (Huez et al. (1998) Mol Cell Biol 18(11):6178-90). IRES have also been reported in different viruses such as cardiovirus, rhinovirus, aphthovirus, HCV, Friend murine leukemia virus (FrMLV) and Moloney murine leukemia virus (MoMLV). As used herein, "IRES" encompasses functional variations of IRES sequences as long as the variation is able to promote direct internal ribosome entry to the initiation codon of a cistron. An IRES may be mammalian, viral or protozoan.

The IRES promotes direct internal ribosome entry to the initiation codon of a downstream cistron, leading to cap-independent translation. Thus, the product of a downstream cistron can be expressed from a bicistronic (or multicistronic) mRNA, without requiring either cleavage of a polyprotein or generation of a monocistronic mRNA. Internal ribosome entry sites are approximately 450 nucleotides in length and are characterized by moderate conservation of primary sequence and strong conservation of secondary structure. The most significant primary sequence feature of the IRES is a pyrimidine-rich site whose start is located approximately 25 nucleotides upstream of the 3' end of the IRES. See Jackson et al.(1990).

Three major classes of picornavirus IRES have been identified and characterized: (1) the cardio- and aphthovirus class (for example, the encephalomycarditis virus, Jang et al. (1990) Gene Dev 4:1560-1572); (2) the entero- and rhinovirus class (for example, polioviruses, Borman et al. (1994) EMBO J. 13:314903157); and (3)the hepatitis A virus (HAV) class, Glass et al. (1993) Virol 193:842-852). For the first two classes, two general principles apply. First, most of the 450-nucleotide sequence of the IRES functions to maintain particular secondary and tertiary structures conducive to ribosome binding and translational initiation. Second, the ribosome entry site is an AUG triplet located at the 3' end of the IRES, approximately 25 nucleotides downstream of a conserved oligopyrimidine tract. Translation initiation can occur either at the ribosome entry site (cardioviruses) or at the next downstream AUG (entero/rhinovirus class). Initiation occurs at both sites in aphthoviruses.

HCV and pestiviruses such as bovine viral diarrhea virus (BVDV) or classical swine fever virus (CSFV) have 341 nt and 370 nt long 5'-UTR respectively. These 5'-UTR fragments form similar RNA secondary structures and can have moderately efficient IRES function (Tsukiyama-Kohara et al. (1992) J. Virol. 66:1476-1483; Frolov I et al., (1998) RNA 4:1418-1435). Recent studies showed that both Friend-murine leukemia virus (MLV) 5'-UTR and rat retrotransposon virus-like 30S (VL30) sequences contain IRES structure of retroviral origin (Torrent et al. (1996) Hum Gene Ther 7:603-612).

In eukaryotic cells, translation is normally initiated by the ribosome scanning from the capped mRNA 5' end, under the control of initiation factors. However, several cellular mRNAs have been found to have IRES structure to mediate the cap-independent translation (van der Velde, et al. (1999) Int J Biochem Cell Biol. 31:87-106). Examples are immunoglobulin heavy-chain binding protein (BiP) (Macejak et al. (1991) Nature 353:90-94), antennapedia mRNA of Drosophilan (Oh et al. (1992) Gene and Dev 6:1643-1653), fibroblast growth factor-2 (FGF-2) (Vagner et al. (1995) Mol Cell Biol 15:35-44), platelet-derived growth factor B (PDGF-B) (Bemstein et al. (1997) J Biol Chem 272:9356-9362), insulin-like growth factor II (Teerink et al. (1995) Biochim Biophys Acta 1264:403-408), and the translation initiation factor eIF4G (Gan et al. (1996) J Biol Chem 271:623-626). Recently, vascular endothelial growth factor (VEGF) was also found to have IRES element (Stein et al. (1998) Mol Cell Biol 18:3112-3119; Huez et al. (1998) Mol Cell Biol 18:6178-6190).

An IRES sequence may be tested and compared to a 2A sequence as shown in Example 1. In one exemplary protocol a test vector or plasmid is generated with one transgene, such as PF4 or VEGF-TRAP, placed under translational control of an IRES, 2A or 2A-like sequence to be tested. A cell is transfected with the vector or palsmid containing the IRES- or 2A-reporter gene sequences and an assay is performed to detect the presence of the transgene. In one illustrative example, the test plasmid comprises co-transcribed PF-4 and VEGF-TRAP coding sequences transcriptionally driven by a CMV promoter wherein the PF-4 or VEGF-TRAP coding sequence is translationally driven by the IRES, 2A or 2A-like sequence to be tested. Host cells are transiently transfected with the test vector or plasmid by means known to those of skill in the art and assayed for the expression of the transgene.

IRES may be prepared using standard recombinant and synthetic methods known in the art. For cloning convenience, restriction sites may be engineered into the ends of the IRES fragments to be used.

To express two or more proteins from a single viral or non-viral vector, an internal ribosome entry site (IRES) sequence is commonly used to drive expression of the second, third, fourth gene, etc. Although the use of an IRES is considered to be the state of the art by many, when two genes are linked via an IRES, the expression level of the second gene is often significantly reduced (Furler et al., Gene Therapy 8:864-873 (2001)). In fact, the use of an IRES to control transcription of two or more genes operably linked to the same promoter can result in lower level expression of the second, third, etc. gene relative to the gene adjacent the promoter. In addition, an IRES sequence may be sufficiently long to present issues with the packaging limit of the vector, e.g., the eCMV IRES has a length of 507 base pairs.

TABLE 1

LITERATURE REFERENCES FOR IRES

| IRES Host | Example | Reference |
|---|---|---|
| Picomavirus | HAV | Glass et al., 1993. Virol 193:842-852 |
| | EMCV | Jang & Wimmer, 1990. Gene Dev 4:1560-1572 |
| | Poliovirus | Borman et al., 1994. EMBO J 13:3149-3157 |
| HCV and pestivirus | HCV | Tsukiyama-Kohara et al., 1992. J Virol 66:1476-1483 |
| | BVDV | Frolov I et al., 1998. RNA. 4:1418-1435 |
| Leishmania virus | LRV-1 | Maga et al., 1995. Mol Cell Biol 15:4884-4889 |
| Retroviruses | MoMLV | Torrent et al., 1996. Hum Gene Ther 7:603-612 |
| | VL30 (Harvey murine sarcoma virus) | |
| | REV | Lopez-Lastra et al., 1997. Hum Gene Ther 8:1855-1865 |
| Eukaryotic mRNA | BiP | Macejak & Sarnow, 1991. Nature 353:90-94 |
| | antennapedia mRNA | Oh et al., 1992. Gene & Dev 6:1643-1653 |
| | FGF-2 | Vagner et al., 1995. Mol Cell Biol 15:35-44 |
| | PDGF-B | Bernstein et al., 1997. J Biol Chem 272:9356-9362 |
| | IGFII | Teerink et al., 1995. Biochim Biophys Acta 1264:403-408 |
| | eIF4G | Gan & Rhoads, 1996. J Biol Chem 271:623-626 |
| | VEGF | Stein et al., 1998. Mol Cell Biol 18:3112-3119; Huez et al., 1998. Mol Cell Biol 18:6178-6190 |

The linking of proteins in the form of polyproteins is a strategy adopted in the replication of many viruses including picomaviridae. Upon translation, virus-encoded self-processing peptides mediate rapid intramolecular (cis) cleavage of the polyprotein to yield discrete mature protein products. The present invention provides advantages over the use of an IRES in that a vector for recombinant protein or polypeptide expression comprising a self-processing peptide (exemplified herein by 2A peptides) is provided which facilitates expression of two or more protein or polypeptide coding sequences using a single promoter, wherein the two or more proteins or polypeptides are expressed in a substantially equimolar ratio.

Self-Prodcessing Cleavage Sites or Sequences

A "self-processing cleavage site" or "self-processing cleavage sequence" as defined above refers to a DNA or amino acid sequence, wherein upon translation, rapid intramolecular (cis) cleavage of a polypeptide comprising the self-processing cleavage site occurs to yield discrete mature protein products. Such a "self-processing cleavage site", may also be referred to as a post-translational or co-translational processing cleavage site, exemplified herein by a 2A site, sequence or domain. A 2A site, sequence or domain demonstrates a translational effect by modifying the activity of the ribosome to promote hydrolysis of an ester linkage, thereby releasing the polypeptide from the translational complex in a manner that allows the synthesis of a discrete downstream translation product to proceed (Donnelly, 2001). Alternatively, a 2A site or domain demonstrates "auto-proteolysis" or "cleavage" by cleaving its own C-terminus in cis to produce primary cleavage products (Furler; Palmenberg, Ann. Rev. Microbiol. 44:603-623 (1990)).

Although the mechanism is not part of the invention, the activity of 2A may involve ribosomal skipping between codons which prevents formation of peptide bonds (de Felipe et al., Human Gene Therapy 11:1921-1931 (2000); Donnelyetal., J. Gen. Virol. 82:1013-1025 (2001); although it has been considered that the domain acts more like an autolytic enzyme (Ryan et al., Virol. 173:35-45 (1989)). Studies in which the Foot and Mouth Disease Virus (FMDV) 2A coding region was cloned into expression vectors and transfected into target cells have established that FMDV 2A cleavage of artificial reporter polyproteins is efficient in a broad range of heterologous expression systems (wheat-germ lysate and transgenic tobacco plant (Halpin et al., U.S. Pat. No. 5,846,767 (1998) and Halpin et al., The Plant Journal 17:453-459 (1999)); Hs 683 human glioma cell line (de Felipe et al., Gene Therapy 6:198-208 (1999); hereinafter referred to as "de Felipe II"); rabbit reticulocyte lysate and human HTK-143 cells (Ryan et al., EMBO J. 13:928-933 (1994)); and insect cells (Roosien et al., J. Gen. Virol. 71:1703-1711 (1990)). The FMDV 2A-mediated cleavage of a heterologous polyprotein for a biologically relevant molecule has been shown for IL-12 (p40/p35 heterodimer; Chaplin et al., J. Interferon Cytokine Res. 19:235-241 (1999)). In transfected COS-7 cells, FMDV 2A mediated the cleavage of a p40-2A-p35 polyprotein into biologically functional subunits p40 and p35 having activities associated with IL-12.

The FMDV 2A sequence has been incorporated into retroviral vectors, alone or combined with different IRES sequences to construct bicistronic, tricistronic and tetracistronic vectors. The efficiency of 2A-mediated gene expression in animals was demonstrated by Furler (2001) using recombinant adeno-associated viral (AAV) vectors encoding α-synuclein and EGFP or Cu/Zn superoxide dismutase (SOD-1) and EGFP linked via the FMDV 2A sequence. EGFP and α-synuclein were expressed at substantially higher levels from vectors which included a 2A sequence relative to corresponding IRES-based vectors, while SOD-1 was expressed at comparable or slightly higher levels. Furler also demonstrated that the 2A sequence results in bicistronic gene expression in vivo after injection of 2A-containing AAV vectors into rat substantia nigra.

For the present invention, the DNA sequence encoding a self-processing cleavage site is exemplified by viral sequences derived from a picomavirus, including but not limited to an entero-, rhino-, cardio-, aphtho- or Foot-and-Mouth Disease Virus (FMDV). In a preferred embodiment, the self-processing cleavage site coding sequence is derived from a FMDV. Self-processing cleavage sites include but are not limited to 2A and 2A-like domains (Donnelly et al., J. Gen. Virol. 82:1027-1041 (2001), expressly incorporated by reference in its entirety.

Positional subcloning of a 2A sequence between two or more heterologous DNA sequences for the inventive vector construct allows the delivery and expression of two or more genes through a single expression vector. Preferably, self processing cleavage sites such as FMDV 2A sequences provide a unique means to express and deliver from a single viral vector, two or multiple proteins, polypeptides or peptides which can be individual parts of, for example, an antibody, heterodimeric receptor or heterodimeric protein.

FMDV 2A is a polyprotein region which functions in the FMDV genome to direct a single cleavage at its own C-terminus, thus functioning in cis. The FMDV 2A domain is typically reported to be about nineteen amino acids in length ((LLNFDLLKLAGDVESNPGP (SEQ ID NO: 1); TLNFDLLKLAGDVESNPGP (SEQ ID NO: 2); Ryan et al., J. Gen. Virol. 72:2727-2732 (1991)), however oligopeptides of as few as fourteen amino acid residues ((LLKLAGDVESNPGP (SEQ ID NO: 3)) have been shown to mediate cleavage at the 2A C-terminus in a fashion similar to its role in the native FMDV polyprotein processing.

Variations of the 2A sequence have been studied for their ability to mediate efficient processing of polyproteins (Donnelly M L L et al. 2001). Homologues and variants of a 2A sequence are included within the scope of the invention and include but are not limited to the sequences presented in Table 2, below:

TABLE 2

Table of Exemplary 2A Sequences

| | |
|---|---|
| LLNFDLLKLAGDVESNPGP | (SEQ ID NO:1) |
| TLNFDLLKLAGDVESNPGP; | (SEQ ID NO:2) |
| LLKLAGDVESNPGP | (SEQ ID NO:3) |
| NFDLLKLAGDVESNPGP | (SEQ ID NO:4) |
| QLLNFDLLKLAGDVESNPGP | (SEQ ID NO:5) |
| APVKQTLNFDLLKLAGDVESNPGP. | (SEQ ID NO:6) |
| VTELLYRMKRAETYCPRPLLAIHPTEARHKQKIVAPV KQTLNFDLLKLAGDVESNPGP | (SEQ ID NO:7) |
| LLAIHPTEARHKQKIVAPVKQTLNFDLLKLAGDVESN PGP | (SEQ ID NO:8) |
| EARHKQKIVAPVKQTLNFDLLKLAGDVESNPGP | (SEQ ID NO:9) |

Distinct advantages of 2A sequences and variants thereof are their use in generating vectors expressing self-processing polyproteins. This invention includes any vector (plasmid or viral based) which includes the coding sequence for proteins or polypeptides linked via self-processing cleavage sites such that the individual proteins are expressed in equimolar or close to equimolar amounts following the cleavage of the polyprotein due to the presence of the self-processing cleavage site, e.g., a 2A domain. These proteins may be heterologous to the vector itself, to each other or to the self-processing cleavage site, e.g., FMDV, thus the self-processing cleavage sites for use in practicing the invention do not discriminate between heterologous proteins and coding sequences derived from the same source as the self-processing cleavage site, in the ability to function or mediate cleavage.

The small size of the 2A coding sequence further enables its use in vectors with a limited packing capacity for a coding sequence such as MV. The utility of AAV vectors can be further expanded since the 2A sequence eliminates the need for dual promoters. The expression levels of individual proteins, polypeptides or peptides from a promoter driving a single open reading frame comprising more than two coding sequences are closer to equimolar as compared to expression levels achievable using IRES sequences or dual promoters. Elimination of dual promoters reduces promoter interference that may result in reduced and/or impaired levels of expression for each coding sequence.

In one preferred embodiment, the FMDV 2A sequence included in a vector according to the invention encodes amino acid residues comprising LLNFDLLKLAGDVESNPGP (SEQ ID NO:1). Alternatively, a vector according to the invention may encode amino acid residues for other 2A-like regions as discussed in Donnelly et al., J. Gen. Virol. 82:1027-1041 (2001) and including but not limited to a 2A-like domain from picomavirus, insect virus, Type C rotavirus, trypanosome repeated sequences or the bacterium, Thermatoga maritima.

The invention contemplates use of nucleic acid sequence variants that encodes a 2A or 2A-like polypeptide, such as a nucleic acid coding sequence for a 2A or 2A-like polypeptide which has a different codon for one or more of the amino acids relative to that of the parent nucleotide. Such variants are specifically contemplated and encompassed by the present invention. Sequence variants of 2A peptides and polypeptides are included within the scope of the invention as well.

As used herein, the term "sequence identity" means nucleic acid or amino acid sequence identity in two or more aligned sequences, when aligned using a sequence alignment program. The term "% homology" is used interchangeably herein with the term "% identity" herein and refers to the level of nucleic acid or amino acid sequence identity between two or more aligned sequences, when aligned using a sequence alignment program. For example, as used herein, 80% homology means the same thing as 80% sequence identity determined by a defined algorithm, and accordingly a homologue of a given sequence has greater than 80% sequence identity over a length of the given sequence.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), by the BLAST algorithm, Altschul et al., J Mol. Biol. 215:403-410 (1990), with software that is publicly available through the National Center for Biotechnology Information (http://www.ncbi.nlm.nih.gov/), or by visual inspection (see generally, Ausubel et al., infra). For purposes of the present invention, optimal alignment of sequences for comparison is most preferably conducted by the local homology algorithm of Smith & Waterman, Adv. Appl. Math. 2:482 (1981). See, also, Altschul, S. F. et al., 1990 and Altschul, S. F. et al., 1997.

The terms "identical" or percent "identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the sequence comparison algorithms described herein, e.g. the Smith-Waterman algorithm, or by visual inspection.

In accordance with the present invention, also encompassed are sequence variants which encode self-processing cleavage polypeptides and polypeptides themselves that have 80, 85, 88, 89, 90, 91, 92, 93, 94, 95, 96, 97, 98, 99% or more sequence identity to the native sequence.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5-10° below the Tm; "intermediate stringency" at about 10-20° below the Tm of the probe; and "low stringency" at about 20-25° below the Tm. Functionally, maximum stringency conditions may be used to identify sequences having strict identity or near-strict identity with the hybridization probe; while high stringency conditions are used to identify sequences having about 80% or more sequence identity with the probe.

Moderate and high stringency hybridization conditions are well known in the art (see, for example, Sambrook, et al, 1989, Chapters 9 and 11, and in Ausubel, F. M., et al., 1993. An example of high stringency conditions includes hybridization at about 42° C. in 50% formamide, 5×SSC, 5× Denhardt's solution, 0.5% SDS and 100 µg/ml denatured carrier DNA followed by washing two times in 2×SSC and 0.5% SDS at room temperature and two additional times in 0.1× SSC and 0.5% SDS at 42° C. 2A sequence variants that encode a polypeptide with the same biological activity as the 2A polypeptides described herein and hybridize under moderate to high stringency hybridization conditions are considered to be within the scope of the present invention.

As a result of the degeneracy of the genetic code, a number of coding sequences can be produced which encode the same 2A or 2A-like polypeptide. For example, the triplet CGT encodes the amino acid arginine. Arginine is alternatively encoded by CGA, CGC, CGG, AGA, and AGG. Therefore it is appreciated that such substitutions in the coding region fall within the sequence variants that are covered by the present invention.

It is further appreciated that such sequence variants may or may not hybridize to the parent sequence under conditions of high stringency. This would be possible, for example, when the sequence variant includes a different codon for each of the amino acids encoded by the parent nucleotide. Such variants are, nonetheless, specifically contemplated and encompassed by the present invention.

Removal of Self-Processing Peptide Sequences.

One concern associated with the use of self-processing peptides, such as 2A or 2A-like sequences is that the N terminus of the first polypeptide contains amino acids derived from the self-processing peptide, i.e. 2A-derived amino acid residues. These amino acid residues are "foreign" to the host and may elicit an immune response when the recombinant protein is expressed or delivered in vivo (i.e., expressed from a viral or non-viral vector in the context of gene therapy or administered as an in vitro-produced recombinant protein). In addition, if not removed, 2A-derived amino acid residues may interfere with protein secretion in producer cells and/or alter protein conformation, resulting in a less than optimal expression level and/or reduced biological activity of the recombinant protein.

The invention includes gene expression constructs, engineered such that an additional proteolytic cleavage site is provided between a polypeptide coding sequence and the self processing cleavage site (i.e., a 2A-sequence) as a means for removal of remaining self processing cleavage site derived amino acid residues following cleavage.

Examples of additional proteolytic cleavage sites are furin cleavage sites with the consensus sequence RXK(R)R (SEQ ID NO: 10), which can be cleaved by endogenous subtilisin-like proteases, such as furin and other serine proteases within the protein secretion pathway. As shown in Example 5, the inventors have demonstrated that 2A residues at the N terminus of the first protein can be efficiently removed by introducing a furin cleavage site RAKR (SEQ ID NO: 15) between the first polypeptide and the 2A sequence. In addition, use of a plasmid containing a 2A sequence and a furin cleavage site adjacent to the 2A site was shown to result in a higher level of protein expression than a plasmid containing the 2A sequence alone. This improvement provides a further advantage in that when 2A residues are removed from the N-terminus of the protein, longer 2A- or 2A like sequences or other self-processing sequences can be used. Such longer self-processing sequences such as 2A- or 2A like sequences may facilitate better equimolar expression of two or more polypeptides by way of a single promoter.

It is advantageous to employ antibodies or analogues thereof with fully human characteristics. These reagents avoid the undesired immune responses induced by antibodies or analogues originating from non-human species. To address possible host immune responses to amino acid residues derived from self-processing peptides, the coding sequence for a proteolytic cleavage site may be inserted (using standard methodology known in the art) between the coding sequence for the first protein and the coding sequence for the self-processing peptide so as to remove the self-processing peptide sequence from the expressed polypeptide, i.e. the antibody. This finds particular utility in therapeutic or diagnostic antibodies for use in vivo.

Any additional proteolytic cleavage site known in the art which can be expressed using recombinant DNA technology vectors may be employed in practicing the invention. Exemplary additional proteolytic cleavage sites which can be inserted between a polypeptide or protein coding sequence and a self processing cleavage sequence (such as a 2A sequence) include, but are not limited to a:

a). Furin cleavage site: RXK(R)R (SEQ ID. NO:10);
b). Factor Xa cleavage site: IE(D)GR (SEQ ID. NO:11);
c). Signal peptidase I cleavage site: e.g. LAGFATVAQA (SEQ ID. NO:12); and
d). Thrombin cleavage site: LVPRGS (SEQ ID. NO:13).

Vectors for use in Practicing the Invention

The present invention contemplates the use of any of a variety of vectors for introduction of constructs comprising the coding sequence for two or more polypeptides or proteins and a self processing cleavage sequence into cells. Numerous examples of gene expression vectors are known in the art and may be of viral or non-viral origin. Non-viral gene delivery methods which may be employed in the practice of the invention include but are not limited to plasmids, liposomes, nucleic acid/liposome complexes, cationic lipids and the like.

Viral vectors can efficiently transduce cells and introduce their own DNA into a host cell. In generating recombinant viral vectors, non-essential genes are replaced with a gene encoding a protein or polypeptide of interest. Exemplary vectors include but are not limited to viral and non-viral vectors, such a retroviral vector (including lentiviral vectors), adenoviral (Ad) vectors including replication competent, replication deficient and gutless forms thereof, adeno-associated virus (AAV) vectors, simian virus 40 (SV-40) vectors, bovine papilloma vectors, Epstein-Barr vectors, herpes vectors, vaccinia vectors, Moloney murine leukemia vectors, Harvey murine sarcoma virus vectors, murine mammary tumor virus vectors, Rous sarcoma virus vectors and nonviral plasmids.

The vector typically comprises an origin of replication and the vector may or may not in addition comprise a "marker" or "selectable marker" function by which the vector can be identified and selected. While any selectable marker can be used, selectable markers for use in recombinant vectors are generally known in the art and the choice of the proper selectable marker will depend on the host cell. Examples of selectable marker genes which encode proteins that confer resistance to antibiotics or other toxins include, but are not limited to ampicillin, methotrexate, tetracycline, neomycin (Southern et al., J., J Mol Appl Genet. 1982;1(4):327-41 (1982)), mycophenolic acid (Mulligan et al., Science 209:1422-7 (1980)), puromycin, zeomycin, hygromycin (Sugden et al., Mol Cell Biol. 5(2):410-3 (1985)) and G418. As will be understood by those of skill in the art, expression vectors typically include an origin of replication, a promoter operably linked to the coding sequence or sequences to be expressed, as well as ribosome binding sites, RNA splice sites, a polyadenylation site, and transcriptional terminator sequences, as appropriate to the coding sequence(s) being expressed.

Reference to a vector or other DNA sequences as "recombinant" merely acknowledges the operable linkage of DNA sequences which are not typically operably linked as isolated from or found in nature. Regulatory (expression and/or control) sequences are operatively linked to a nucleic acid coding sequence when the expression and/or control sequences regulate the transcription and, as appropriate, translation of the nucleic acid sequence. Thus expression and/or control sequences can include promoters, enhancers, transcription terminators, a start codon (i.e., ATG) 5' to the coding sequence, splicing signals for introns and stop codons.

Adenovirus gene therapy vectors are known to exhibit strong transient expression, excellent titer, and the ability to transduce dividing and non-dividing cells in vivo (Hitt et al., Adv in Virus Res 55:479-505 (2000)). The recombinant Ad vectors of the instant invention comprise: (1) a packaging site enabling the vector to be incorporated into replication-defective Ad virions; (2) the coding sequence for two or more polypeptides or proteins of interest, e.g., heavy and light chains of an immunoglobulin of interest; and (3) a sequence encoding a self-processing cleavage site alone or in combination with an additional proteolytic cleavage site. Other elements necessary or helpful for incorporation into infectious virions, include the 5' and 3' Ad ITRs, the E2 genes, portions of the E4 gene and optionally the E3 gene.

Replication-defective Ad virions encapsulating the recombinant Ad vectors of the instant invention are made by standard techniques known in the art using Ad packaging cells and packaging technology. Examples of these methods may be found, for example, in U.S. Pat. No. 5,872,005. The coding sequence for two or more polypeptides or proteins of interest is commonly inserted into adenovirus in the deleted E3 region of the virus genome. Preferred adenoviral vectors for use in practicing the invention do not express one or more wild-type Ad gene products, e.g., E1a, E1b, E2, E3, and E4. Preferred embodiments are virions that are typically used together with packaging cell lines that complement the functions of E1, E2A, E4 and optionally the E3 gene regions. See, e.g. U.S. Pat. Nos. 5,872,005, 5,994,106, 6,133,028 and 6,127,175. Thus, as used herein, "adenovirus" and "adenovirus particle" refer to the virus itself or derivatives thereof and cover all serotypes and subtypes and both naturally occurring and recombinant forms, except where indicated otherwise. Such adenoviruses may be wildtype or may be modified in various ways known in the art or as disclosed herein. Such modifications include modifications to the adenovirus genome that is packaged in the particle in order to make an infectious virus. Such modifications include deletions known in the art, such as deletions in one or more of the E1a, E1b, E2a, E2b, E3, or E4 coding regions. Exemplary packaging and producer cells are derived from 293, A549 or HeLa cells. Adenovirus vectors are purified and formulated using standard techniques known in the art.

Adeno-associated virus (AAV) is a helper-dependent human parvovirus which is able to infect cells latently by chromosomal integration. Because of its ability to integrate chromosomally and its nonpathogenic nature, AAV has significant potential as a human gene therapy vector. For use in practicing the present invention rAAV virions may be produced using standard methodology, known to those of skill in the art and are constructed such that they include, as operatively linked components in the direction of transcription, control sequences including transcriptional initiation and termination sequences, and the coding sequence(s) of interest. More specifically, the recombinant AAV vectors of the instant invention comprise: (1) a packaging site enabling the vector to be incorporated into replication-defective AAV virions; (2) the coding sequence for two or more polypeptides or proteins of interest, e.g., heavy and light chains of an immunoglobulin of interest; (3) a sequence encoding a self-processing cleavage site alone or in combination with an additional proteolytic cleavage site. AAV vectors for use in practicing the invention are constructed such that they also include, as operatively linked components in the direction of transcription, control sequences including transcriptional initiation and termination sequences. These components are flanked on the 5' and 3' end by functional AAV ITR sequences. By "functional AAV ITR sequences" is meant that the ITR sequences function as intended for the rescue, replication and packaging of the AAV virion.

Recombinant AAV vectors are also characterized in that they are capable of directing the expression and production of selected recombinant polypeptide or protein products in target cells. Thus, the recombinant vectors comprise at least all of the sequences of AAV essential for encapsidation and the physical structures for infection of the recombinant AAV (rAAV) virions. Hence, AAV ITRs for use in the vectors of the invention need not have a wild-type nucleotide sequence (e.g., as described in Kotin, Hum. Gene Ther., 5:793-801, 1994), and may be altered by the insertion, deletion or substitution of nucleotides or the AAV ITRs may be derived from any of several AAV serotypes. Generally, an AAV vector is a vector derived from an adeno-associated virus serotype, including without limitation, AAV-1, AAV-2, AAV-3, AAV-4, AAV-5, AAV-6, AAV-7, AAV-8, etc. Preferred rAAV vectors have the wild type REP and CAP genes deleted in whole or part, but retain functional flanking ITR sequences.

Typically, an AAV expression vector is introduced into a producer cell, followed by introduction of an AAV helper construct, where the helper construct includes AAV coding regions capable of being expressed in the producer cell and which complement AAV helper functions absent in the AAV vector. The helper construct may be designed to down regulate the expression of the large Rep proteins (Rep78 and Rep68), typically by mutating the start codon following p5 from ATG to ACG, as described in U.S. Pat. No. 6,548,286, expressly incorporated by reference herein. This is followed by introduction of helper virus and/or additional vectors into the producer cell, wherein the helper virus and/or additional vectors provide accessory functions capable of supporting efficient rAAV virus production. The producer cells are then cultured to produce rAAV. These steps are carried out using standard methodology. Replication-defective AAV virions encapsulating the recombinant AAV vectors of the instant invention are made by standard techniques known in the art using AAV packaging cells and packaging technology. Examples of these methods may be found, for example, in U.S. Pat. Nos. 5,436,146; 5,753,500, 6,040,183, 6,093,570 and 6,548,286, expressly incorporated by reference herein in their entirety. Further compositions and methods for packaging are described in Wang et al. (US 2002/0168342), also incorporated by reference herein in its entirety and include those techniques within the knowledge of those of skill in the art.

In practicing the invention, host cells for producing rAAV virions include mammalian cells, insect cells, microorganisms and yeast. Host cells can also be packaging cells in which the AAV rep and cap genes are stably maintained in the host cell or producer cells in which the AAV vector genome is stably maintained and packaged. Exemplary packaging and producer cells are derived from 293, A549 or HeLa cells. AAV vectors are purified and formulated using standard techniques known in the art.

Retroviral vectors are also a common tool for gene delivery (Miller, 1992, Nature 357: 455-460). Retroviral vectors and more particularly lentiviral vectors may be used in practicing the present invention. Accordingly, the term "retrovirus" or "retroviral vector", as used herein is meant to include "lentivirus" and "lentiviral vectors" respectively. Retroviral vectors have been tested and found to be suitable delivery vehicles for the stable introduction of genes of interest into the genome of a broad range of target cells. The ability of retroviral vectors to deliver unrearranged, single copy transgenes into cells makes retroviral vectors well suited for transferring genes into cells. Further, retroviruses enter host cells by the binding of retroviral envelope glycoproteins to specific cell surface receptors on the host cells. Consequently, pseudotyped retroviral vectors in which the encoded native envelope protein is replaced by a heterologous envelope protein that has a different cellular specificity than the native envelope protein (e.g., binds to a different cell-surface receptor as compared to the native envelope protein) may also find utility in practicing the present invention. The ability to direct the delivery of retroviral vectors encoding one or more target protein coding sequences to specific target cells is desirable in practice of the present invention.

The present invention provides retroviral vectors which include e.g., retroviral transfer vectors comprising one or more transgene sequences and retroviral packaging vectors comprising one or more packaging elements. In particular, the present invention provides pseudotyped retroviral vectors encoding a heterologous or functionally modified envelope protein for producing pseudotyped retrovirus.

The core sequence of the retroviral vectors of the present invention may be readily derived from a wide variety of retroviruses, including for example, B, C, and D type retroviruses as well as spumaviruses and lentiviruses (see RNA Tumor Viruses, Second Edition, Cold Spring Harbor Laboratory, 1985). An example of a retrovirus suitable for use in the compositions and methods of the present invention includes, but is not limited to, lentivirus. Other retroviruses suitable for use in the compositions and methods of the present invention include, but are not limited to, Avian Leukosis Virus, Bovine Leukemia Virus, Murine Leukemia Virus, Mink-Cell Focus-Inducing Virus, Murine Sarcoma Virus, Reticuloendotheliosis virus and Rous Sarcoma Virus. Particularly preferred Murine Leukemia Viruses include 4070A and 1504A (Hartley and Rowe, J. Virol. 19:19-25, 1976), Abelson (ATCC No. VR-999), Friend (ATCC No. VR-245), Graffi, Gross (ATCC No. VR-590), Kirsteni Harvey Sarcoma Virus and Rauscher (ATCC No. VR-998), and Moloney Murine Leukemia Virus (ATCC No. VR-190). Such retroviruses may be readily obtained from depositories or collections such as the American Type Culture Collection ("ATCC"; Rockville, Md.), or isolated from known sources using commonly available techniques.

Preferably, a retroviral vector sequence of the present invention is derived from a lentivirus. A preferred lentivirus is a human immunodeficiency virus, e.g., type 1 or 2 (i.e., HIV-1 or HIV-2, wherein HIV-1 was formerly called lymphadenopathy associated virus 3 (HTLV-III) and acquired immune deficiency syndrome (AIDS)-related virus (ARV)), or another virus related to HIV-1 or HIV-2 that has been identified and associated with AIDS or AIDS-like disease. Other lentivirus include, a sheep Visna/maedi virus, a feline immunodeficiency virus (FIV), a bovine lentivirus, simian immunodeficiency virus (SIV), an equine infectious anemia virus (EIAV), and a caprine arthritis-encephalitis virus (CAEV).

The various genera and strains of retroviruses suitable for use in the compositions and methods are well known in the art (see, e.g., Fields Virology, Third Edition, edited by B. N. Fields et al., Lippincott-Raven Publishers (1996), see e.g., Chapter 58, Retroviridae: The Viruses and Their Replication, Classification, pages 1768-1771, including Table 1, incorporated herein by reference).

The present invention provides retroviral packaging systems for generating producer cells and producer cell lines that produce retroviruses, and methods of making such packaging systems. Accordingly, the present invention also provides producer cells and cell lines generated by introducing a retroviral transfer vector into such packaging systems (e.g., by transfection or infection), and methods of making such packaging cells and cell lines.

The packaging systems of the present invention comprise at least two packaging vectors: a first packaging vector which comprises a first nucleotide sequence comprising a gag, a pol, or gag and pol genes; and a second packaging vector which comprises a second nucleotide sequence comprising a heterologous or functionally modified envelope gene. In a preferred embodiment, the retroviral elements are derived from a lentivirus, such as HIV. Preferably, the vectors lack a functional tat gene and/or functional accessory genes (vif, vpr, vpu, vpx, nef). In another preferred embodiment, the system further comprises a third packaging vector that comprises a nucleotide sequence comprising a rev gene. The packaging system can be provided in the form of a packaging cell that contains the first, second, and, optionally, third nucleotide sequences.

The invention is applicable to a variety of retroviral systems, and those skilled in the art will appreciate the common elements shared across differing groups of retroviruses. The description herein uses lentiviral systems as a representative example. However, all retroviruses share the features of enveloped virions with surface projections and containing one molecule of linear, positive-sense single stranded RNA, a genome consisting of a dimer, and the common proteins gag, pol and env.

Lentiviruses share several structural virion proteins in common, including the envelope glycoproteins SU (gp120) and TM (gp41), which are encoded by the env gene; CA (p24), MA (p17) and NC (p7-11), which are encoded by the gag gene; and RT, PR and IN encoded by the pol gene. HIV-1 and HIV-2 contain accessory and other proteins involved in regulation of synthesis and processing virus RNA and other replicative functions. The accessory proteins, encoded by the vif, vpr, vpu/vpx, and nef genes, can be omitted (or inactivated) from the recombinant system. In addition, tat and rev can be omitted or inactivated, e.g., by mutation or deletion.

First generation lentiviral vector packaging systems provide separate packaging constructs for gag/pol and env, and typically employ a heterologous or functionally modified envelope protein for safety reasons. In second generation lentviral vector systems, the accessory genes, vif, vpr, vpu and nef, are deleted or inactivated. Third generation lentiviral vector systems are those from which the tat gene has been deleted or otherwise inactivated (e.g., via mutation).

Compensation for the regulation of transcription normally provided by tat can be provided by the use of a strong constitutive promoter, such as the human cytomegalovirus immediate early (HCAAV-IE) enhancer/promoter. Other promoters/enhancers can be selected based on strength of constitutive promoter activity, specificity for target tissue (e.g., a liver-specific promoter), or other factors relating to desired control over expression, as is understood in the art. For example, in some embodiments, it is desirable to employ an inducible promoter such as tet to achieve controlled expression. The gene encoding rev is preferably provided on a separate expression construct, such that a typical third generation lentviral vector system will involve four plasmids: one each for gagpol, rev, envelope and the transfer vector. Regardless of the generation of packaging system employed, gag and pol can be provided on a single construct or on separate constructs.

Typically, the packaging vectors are included in a packaging cell, and are introduced into the cell via transfection, transduction or infection. Methods for transfection, transduction or infection are well known by those of skill in the art. A retroviral transfer vector of the present invention can be introduced into a packaging cell line, via transfecton, transduction or infection, to generate a producer cell or cell line. The packaging vectors of the present invention can be introduced into human cells or cell lines by standard methods including, e.g., calcium phosphate transfection, lipofection orelectroporabon. In some embodiments, the packaging vectors are introduced into the cells together with a dominant selectable marker, such as neo, DHFR, Gln synthetase or ADA, followed by selection in the presence of the appropriate drug and isolation of clones. A selectable marker gene can be linked physically to genes encoding by the packaging vector.

Stable cell lines, wherein the packaging functions are configured to be expressed by a suitable packaging cell, are known. For example, see U.S. Pat. No. 5,686,279; and Ory et al., Proc. Natl. Acad. Sci. (1996) 93:11400-11406, which describe packaging cells. Further description of stable cell line production can be found in Dull et al., 1998, J. Virology 72(11):8463-8471; and in Zufferey et al., 1998, J. Virology 72(12):9873-9880

Zufferey et al., 1997, Nature Biotechnology 15:871-875, teach a lentiviral packaging plasmid wherein sequences 3' of pol including the HIV-1 envelope gene are deleted. The construct contains tat and rev sequences and the 3' LTR is replaced with poly A sequences. The 5' LTR and psi sequences are replaced by another promoter, such as one which is inducible. For example, a CMV promoter or derivative thereof can be used.

The packaging vectors of interest may contain additional changes to the packaging functions to enhance lentiviral protein expression and to enhance safety. For example, all of the HIV sequences upstream of gag can be removed. Also, sequences downstream of the envelope can be removed. Moreover, steps can be taken to modify the vector to enhance the splicing and translation of the RNA.

Optionally, a conditional packaging system is used, such as that described by Dull et al., J. Virology 72(11):8463-8471, 1998. Also preferred is the use of a self-inactivabng vector (SIN), which improves the biosafety of the vector by deletion of the HIV-1 long terminal repeat (LTR) as described, for example, by Zufferey et al., 1998, J. Virology 72(12):9873-9880. Inducible vectors can also be used, such as through a tet-inducible LTR.

The vectors of the invention typically include hetemlogous control sequences, which include, but are not limited to, constitutive promoters, such as the cytomegalovirus (CMV) immediate early promoter, the RSV LTR, the MOMLV LTR, and the PGK promoter; tissue or cell type specific promoters including mTTR, TK, HBV, hAAT, regulatable or inducible promoters, enhancers, etc. Preferred promoters include the LSP promoter (III et al., Blood Coagul. Fibrinolysis 8S2:23-30 (1997)), the EF1-alpha promoter (Kim et al., Gene 91(2): 217-23 (1990)) and Guo et al., Gene Ther. 3(9):802-10 (1996)). Most preferred promoters include the elongation factor 1-alpha (EF1a) promoter, a phosphoglycerate kinase-1 (PGK) promoter, a cytomegalovirus immediate early gene (CMV) promoter, chimeric liver-specific promoters (LSPs), a cytomegalovirus enhancer/chicken beta-actin (CAG) promoter, a tetracycline responsive promoter (TRE), a transthyretin promoter (TTR), an simian virus 40 (SV40) promoter and a CK6 promoter. The sequences of these and numerous additional promoters are known in the art. The relevant sequences may be readily obtained from public databases and incorporated into vectors for use in practicing the present invention.

The present invention also contemplates the inclusion of a gene regulation system for the controlled expression of the coding sequence for two or more polypeptides or proteins of interest. Gene regulation systems are useful in the modulated expression of a particular gene or genes. In one exemplary approach, a gene regulation system or switch includes a chimeric transcription factor that has a ligand binding domain, a transcriptional activation domain and a DNA binding domain. The domains may be obtained from virtually any source and may be combined in any of a number of ways to obtain a novel protein. A regulatable gene system also includes a DNA response element which interacts with the chimeric transcription factor. This element is located adjacent to the gene to be regulated.

Exemplary gene regulation systems that may be employed in practicing the present invention include, the Drosophila ecdysone system (Yao et al., Proc. Nat. Acad. Sci., 93:3346 (1996)), the Bombyx ecdysone system (Suhr et al., Proc. Nat. Acad. Sci., 95:7999 (1998)), the Valentis GeneSwitch® synthetic progesterone receptor system which employs RU486 as the inducer (Osterwalder et al., Proc Natl Acad Sci 98(22): 12596-601 (2001)); the Tet™ & RevTet™ Systems (BD Biosciences Clontech), which employs small molecules, such as tetracycline (Tc) or analogues, e.g. doxycycline, to regulate (turn on or off) transcription of the target (Knott et al., Biotechniques 32(4):796, 798, 800 (2002)); ARIAD Regulation Technology which is based on the use of a small molecule to bring together two intracellular molecules, each of which is linked to either a transcriptional activator or a DNA binding protein. When these components come together, transcription of the gene of interest is activated. Ariad has two major systems: a system based on homodimerizabon and a system based on heterodimerization (Rivera et al., Nature Med, 2(9): 1028-1032 (1996); Ye et al., Science 283:88-91 (2000)).

Preferred gene regulation systems for use in practicing the present invention are the ARIAD Regulation Technology and the Tet™ & RevTet™ Systems.

Delivery of Nucleic Acid Constructs Including Immunoglobulin Coding Sequences to Cells The vector constructs of the invention comprising nucleic acid sequences encoding antibodies or fragments thereof or other heterologous proteins in the form of self-processing recombinant polypeptides may be introduced into cells in vitro, ex vivo or in vivo for delivery of foreign, therapeutic or transgenes to cells, e.g., somatic cells, or in the production of recombinant polypepbdes by vector-transduced cells.

The vector constructs of the invention may be introduced into cells in vitro or ex vivo using standard methodology known in the art. Such techniques include transfecton using calcium phosphate, microinjection into cultured cells (Capecchi, Cell 22:479-488 (1980)), electroporation (Shigekawa et al., BioTechn., 6:742-751 (1988)), liposome-mediated gene transfer (Mannino et al., BioTechn., 6:682-690 (1988)), lipid-mediated transduction (Feigner et al., Proc. Natl. Acad. Sci. USA 84:7413-7417 (1987)), and nucleic acid delivery using high-velocity microprojectiles (Klein et al., Nature 327:70-73 (1987)).

For in vitro or ex vivo expression, any cell effective to express a functional protein product may be employed. Numerous examples of cells and cell lines used for protein expression are known in the art. For example, prokaryotic cells and insect cells may be used for expression. In addition, eukaryotic microorganisms, such as yeast may be used. The expression of recombinant proteins in prokaryotic, insect and yeast systems are generally known in the art and may be adapted for antibody expression using the compositions and methods of the present invention.

Examples of cells useful for expression further include mammalian cells, such as fibroblast cells, cells from non-human mammals such as ovine, porcine, murine and bovine cells, insect cells and the like. Specific examples of mammalian cells include COS cells, VERO cells, HeLa cells, Chinese hamster ovary (CHO) cells, 293 cell, NSO cells, 3T3 fibroblast cells, W138 cells, BHK cells, HEPG2 cells, DUX cells and MDCK cells.

Host cells are cultured in conventional nutrient media, modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are typically suitable for culturing host cells. A given medium is generally supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The appropriate culture conditions for a particular cell line, such as temperature, pH and the like, are generally known in the art, with suggested culture conditions for culture of numerous cell lines for example in the ATCC Catalogue available on line at "http:/www.atcc.org/SearchCatalogs/AllCollections.cfm"

The vectors may be administered in vivo via various routes (e.g., intradermally, intravenously, intratumorally, into the brain, intraportally, intraperitoneally, intramuscularly, into the bladder etc.), to deliver multiple genes connected via a self processing cleavage sequence to express two or more proteins or polypeptides in animal models or human subjects. Dependent upon the route of administration, the therapeutic proteins elicit their effect locally (in brain or bladder) or systemically (other routes of administration). The use of tissue specific promoters 5' to the open reading frame(s) results in tissue specific expression of the proteins or polypeptides encoded by the entire open reading frame.

Various methods that introduce a recombinant vector carrying a transgene into target cells in vitro, ex vivo or in vivo have been previously described and are well known in the art. The present invention provides for therapeutic methods, vaccines, and cancer therapies by infecting targeted cells with the recombinant vectors containing the coding sequence for two or more proteins or polypeptides of interest, and expressing the proteins or polypeptides in the targeted cell.

For example, in vivo delivery of the recombinant vectors of the invention may be targeted to a wide variety of organ types including, but not limited to brain, liver, blood vessels, muscle, heart, lung and skin.

In the case of ex vivo gene transfer, the target cells are removed from the host and genetically modified in the laboratory using recombinant vectors of the present invention and methods well known in the art.

The recombinant vectors of the invention can be administered using conventional modes of administration including but not limited to the modes described above. The recombinant vectors of the invention may be in a variety of formulations which include but are not limited to liquid solutions and suspensions, microvesicles, liposomes and injectable or infusible solutions. The preferred form depends upon the mode of administration and the therapeutic application.

The many advantages to be realized in using the inventive recombinant vector constructs of the invention in immunoglobulin production in vivo include administration of a single vector for long-term and sustained antibody expression in patients; in vivo expression of an antibody or fragment thereof having full biological activities; and the natural post-translabonal modifications of the antibody generated in human cells.

The recombinant vector constructs of the present invention find further utility in the in vitro production of recombinant antibodies for use in therapy. Methods for recombinant protein production are well known in the art and may be utilized for expression of recombinant antibodies using the self processing cleavage site-containing vector constructs described herein.

In one aspect, the invention provides methods for producing a recombinant immunoglobulin or fragment thereof, by introducing an expression vector such as described above into a cell to obtain a transfected cell, wherein the vector comprises in the 5' to 3' direction: a promoter operably linked to the coding sequence for an immunoglobulin heavy or light chain or fragment thereof, a self processing sequence such as a 2A or 2A-like sequence and the coding sequence for an immunoglobulin heavy or light chain or a fragment thereof, wherein the self processing cleavage sequence is inserted between the first and second immunoglobulin coding sequences. It will be appreciated that the coding sequence for either the immunoglobulin heavy chain or the coding sequence for the immunoglobulin light chain may be 5' to the 2A sequence (i.e. first) in a given vector construct.

In a related aspect, the invention provides a method for producing a recombinant immunoglobulin or fragment thereof, by introducing an expression vector such as described above into a cell, wherein the vector further comprises an additional proteolytic cleavage site between the first and second immunoglobulin coding sequences. A preferred additional proteolytic cleavage site is a furin cleavage site with the consensus sequence RXK(R)R (SEQ ID NO:10).

In one exemplary aspect of the invention, vector introduction or administration to a cell is followed by one or more of the following steps:

(1) culturing the transfected cell under conditions for selecting a cell expressing the immunoglobulin or fragment thereof;

(2) measuring expression of the immunoglobulin or the fragment thereof; and (3) collecting the immunoglobulin or the fragment thereof.

Another aspect of the invention provides a cell for expressing a recombinant immunoglobulin or a fragment thereof, wherein the cell comprises an expression vector for the expression of two or more immunoglobulin chains or fragments thereof, a promoter operably linked to a first coding sequence for an immunoglobulin chain or fragment thereof, a self processing cleavage sequences, such as a 2A or 2A-like sequence, and a second coding sequence for an immunoglobulin chain or a fragment thereof, wherein the self processing cleavage sequence is inserted between the first and the second coding sequences. In a related aspect, the cell comprises an expression vector as described above wherein the expression vector further comprises an additional proteolytic cleavage site between the first and second immunoglobulin coding sequences. A preferred additional proteolytic cleavage site is a furin cleavage site with the. consensus sequence RXK(R)R (SEQ ID NO:10).

Antibody Production

As used herein, "the coding sequence for a first chain of an immunoglobulin molecule or a fragment thereof" refers to a nucleic acid sequence encoding a protein molecule including, but not limited to a light chain or heavy chain for an antibody or immunoglobulin, or a fragment thereof.

As used herein, a "the coding sequence for a second chain of an immunoglobulin molecule or a fragment thereof" refers to a nucleic acid sequence encoding a protein molecule including, but not limited to a light chain or heavy chain for an antibody or immunoglobulin, or a fragment thereof.

The sequence encoding the first or second chain for an antibody or immunoglobulin or a fragment thereof includes a heavy chain or a fragment thereof for an IgG, IgM, IgD, IgE or IgA. The sequence encoding the chain for an antibody or immunoglobulin or a fragment thereof also includes the light chain or a fragment thereof for an IgG, IgM, IgD, IgE or IgA. Genes for whole antibody molecules as well as modified or derived forms thereof, include fragments like Fab, single chain Fv(scFv) and F(ab')$_2$. The antibodies and fragments can be animal-derived, human-mouse chimeric, humanized, DeImmunized™ or fully human. The antibodies can be bispecific and include but are not limited to diabodies, quadroma, mini-antibodies, ScBs antibodies and knobs-into-holes antibodies.

The production and recovery of the antibodies themselves can be achieved in various ways known in the art (Harlow et al., "Antibodies, A Laboratory Manual", Cold Spring Harbor Lab, (1988)).

In practicing the invention, the production of an antibody or variant (analogue) thereof using recombinant DNA technology can be achieved by culturing a modified recombinant host cell under culture conditions appropriate for the growth of the host cell and the expression of the coding sequences. In order to monitor the success of expression, the antibody levels with respect to the antigen may be monitored using standard techniques such as ELISA, RIA and the like. The antibodies are recovered from the culture supernatant using standard techniques known in the art. Purified forms of these antibodies can, of course, be readily prepared by standard purification techniques, preferably including affinity chromatography via protein A, protein G or protein L columns, or with respect to the particular antigen, or even with respect to the particular epitope of the antigen for which specificity is desired. Antibodies can also be purified with conventional chromatography, such as an ion exchange or size exclusion column, in conjunction with other technologies, such as ammonia sulfate precipitation and size-limited membrane filtration. Preferred expression systems are designed to include signal peptides so that the resulting antibodies are secreted into the culture medium or supernatant, however, intracellular production is also possible.

The production and selection of antigen-specific fully human monoclonal antibodies from mice engineered with human Ig loci, has previously been described (Jakobovits A. et al., Advanced Drug Delivery Reviews Vol. 31, pp: 33-42 (1998); Mendez M, et al., Nature Genetics Vol.15, pp: 146-156 (1997); Jakobovits A. et al., Current Opinion in Biotechnology Vol. 6, No. 5, pp: 561-566 (1995); Green L, et al., Nature Genetics Vol. 7, No. 1, pp: 13-21(1994).

High level expression of therapeutic monoclonal antibodies has been successfully demonstrated in the milk of transgenic goats and it has been shown that antigen binding levels are equivalent to that of monoclonal antibodies produced using conventional, cell culture technology. This method is based on development of human therapeutic proteins in the milk of transgenic animals, which carry genetic information allowing them to express human therapeutic proteins in their milk. Once they are produced, these recombinant proteins can be efficiently purified from milk using standard technology. See e.g., Pollock, D. P. et al., Journal of Immunological Methods. 231:147-157, 1999 and Young, M. W. et al., Res Immunol. July-August; 149(6): 609-610, 1998. Animal milk, egg white, blood, urine, seminal plasma and silk worm cocoons from transgenic animals have demonstrated potential as sources for production of recombinant proteins at an industrial scale (Houdebine L M, Curr Opin Biotechnology, 13:625-629, 2002; Little M et al., Immunol Today, 21(8):364-70, 2000; and Gura T, Nature, 417:584-586, 2002). The invention contemplates use of transgenic animal expression systems for expression of a recombinant an antibody or variant (analogue) thereof using the self-processing cleavage site-encoding vectors of the invention.

Production of recombinant proteins in plants has also been successfully demonstrated including, but not limited to, rice transformed by *Agrobacterium* infection, recombinant human GM-CSF expression in the seeds of transgenic tobacco plants and expression of antibodies including single-chain antibodies in plants. See, e.g., Streatfield S J, Howard J A, Int J Parasitol. 33(5-6):479-93, 2003; Schillberg S. et al., Cell Mol Life Sci. 60(3):433A5, 2003; Pogue G P et al., Annu Rev Phytopathol. 40:45-74, 2002; and McCormick M et al., J Immunological Methods, 278(1-2):95-104, 2003. The invention contemplates use of transgenic plant expression systems for expression of a recombinant immunoglobulin or fragment thereof using the self-processing cleavage site-encoding vectors of the invention.

Baculovirus vector expression systems in conjunction with insect cells are also gaining ground as a viable platform for recombinant protein production. Baculovirus vector expression systems have been reported to provide advantages relative to mammalian cell culture such as ease of culture and higher expression levels. See, e.g., Ghosh S. et al., Mol Ther. July 2002;6(1):5-11, 2002 and Ikonomou L et al., Appl Microbiol Biotechnol. 62(1):1-20, 2003. The invention further contemplates use of Baculovinms vector expression systems for expression of a recombinant immunoglobulin or fragment thereof using the self-processing cleavage site-encoding vectors of the invention.

Yeast-based systems may also be employed for expression of a recombinant immunoglobulin or fragment thereof using the self-processing cleavage site-encoding vectors of the invention. See, e.g., Stuart, W D (1997): "Heterologous dimeric proteins produced in heterokaryons"; U.S. Pat. No. 5,643,745, expressly incorporated by reference herein.

It will be understood that the vectors of the invention which comprise the coding sequence for a self-processing peptide alone or in combination with an additional coding sequence for a proteolytic cleavage site find utility in the expression of recombinant immunoglobulins or fragments thereof in any protein expression system, a number of which are known in the art and examples of which are described herein. One of skill in the art may easily adapt the vectors of the invention for use in any protein expression system.

The objects of the invention have been achieved by a series of experiments, some of which are described by way of the following non-limiting examples.

EXAMPLE 1

Construction of AAV 2A Expression Construct

An AAV vector encoding full length heavy and light chains of a rat anti-FLK-1 monoclonal antibody and a self processing 2A cleavage sequence was constructed. The variable and constant regions of the antibody heavy and light chains were cloned from a cDNA of the parental hydridoma cells using the Polymerase Chain Reaction (PCR). The cDNA was synthesized with reverse transcriptase from total RNA isolated from the hydridoma cells using Qiagen's total RNA purification kit. The nucleotide sequence of the monoclonal antibody was analyzed using an automatic sequencing system (Applied Biosystems) and consensus sequences were obtained from the sequencing data derived from multiple independent PCR reactions.

The DNA fragments that encode the rat antibody heavy chain, 2A sequence and antibody light chain were linked together by PCR extension. Artificial FMDV 2A oligo nucleotides were synthesized based on the 2A peptide sequence APVKQTLNFDLLKLAGDVESNPGP (SEQUENCE ID NO: 6). The heavy and light chain fragments were amplified from the cloned plasmids that encode the full-length antibody heavy and light chains respectively. During the PCR, a Hind III restriction endonucleotidase site was added to the 5' prime end of the heavy chain and a Not I site to the 3' prime end of the light chain. The fused heavy chain—2A—light chain DNA fragment was digested with Hind III and Not I, which was purified from agarose gel. The purified DNA fragment was inserted into an AAV plasmid backbone flanked with Hind III and Not I sites using T4 DNA ligase. AAV constructs containing an EF1-alpha promoter or a CAG promoter driving expression of the antibody heavy chain—2A sequence—light chain were prepared. In variant forms, a native signal peptide (leader) was included in the heavy or light chain, respectively, to facilitate secretion of the polypeptides upon synthesis. In addition, the constructs contain a woodchuck hepatitis virus post-transcriptional regulatory element (WPRE) and poly A sequence to ensure high level gene expression (FIG. 1).

EXAMPLE 2

Expression of a Rat IgG from an AAV H2AL Plasmid Transfected into 293T Cells

Figure 4:
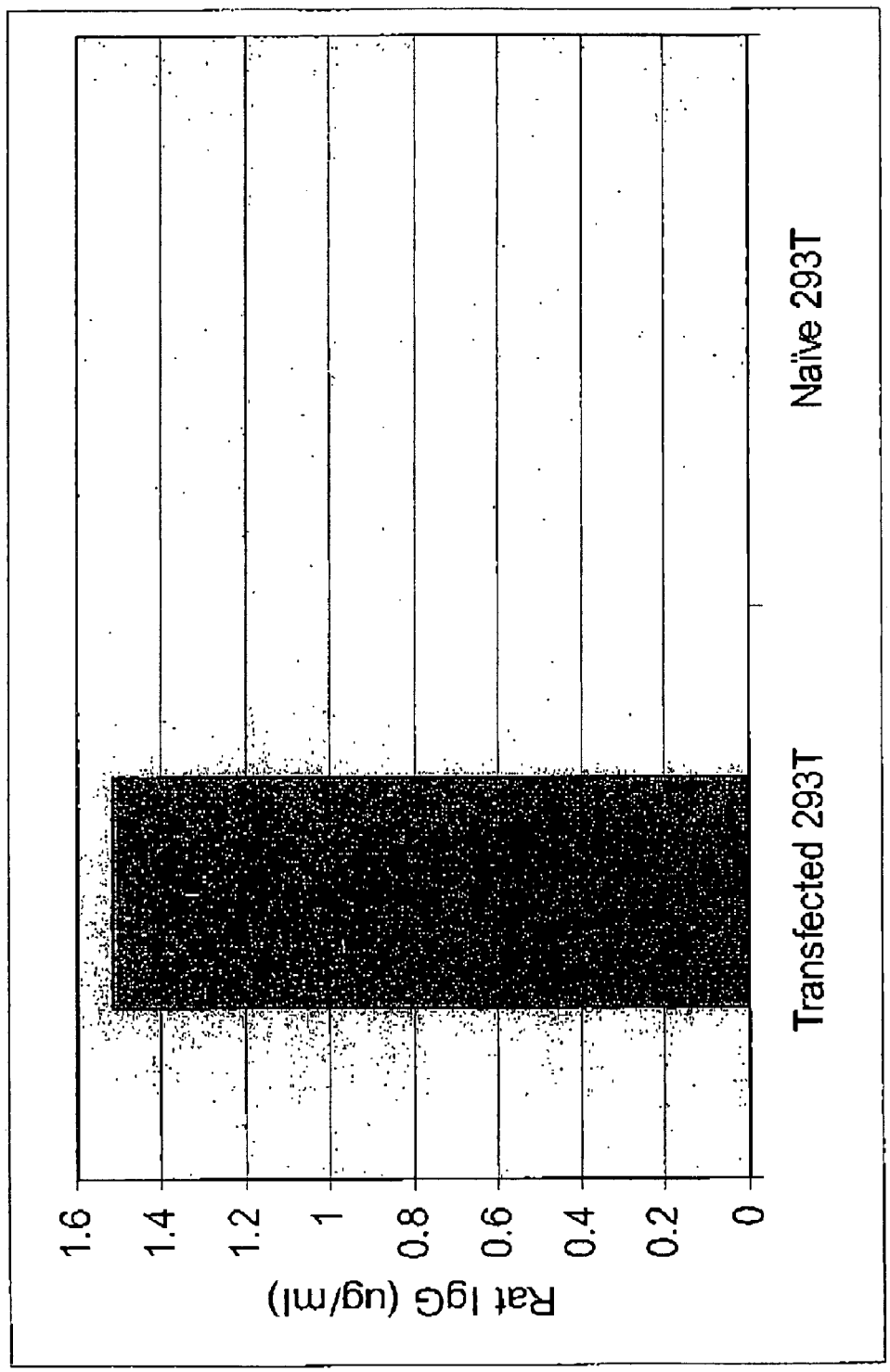
FIG. 4 shows the expression level of a rat anti-FLK-1 monoclonal antibody in the supernatant of 293T cells transfected with anti-FLK-1 Ig/AAV H2AL (heavy chain—2A sequence—light chain) plasmid.

An AAV vector construct (AAV H2AL) encoding the heavy and light chain of a monoclonal IgG antibody against murine FLK-1 and linked by insertion of the FMDV 2A sequence, was transiently transfected into 60% confluent 293T cells. Cells were grown in Iscove's Modified Dulbecco's Medium (IMDM) supplemented with 10% fetal bovine serum, 1% Lglutamine, and 1% penicillin-streptomycin solution (Invitrogen). Transfection was carried out using a FuGENE 6 transfection kit (Roche), containing a lipid-based transfection reagent resulting in uptake of foreign DNA into mammalian cells. AAV H2AL plasmid DNA was mixed with the transfection reagent according to the manufacturer's instruction and the DNA-lipid mixture was added to the cell culture medium. The transfected cells were incubated for 48 or 72 hours and the supematants analyzed for antibody expression. The mAb concentration was determined using a rat IgG ELISA assay (Bethyl Laboratories), in which mAb IgG protein was captured by an immobilized anti-rat IgG antibody on ELISA plates and detected by an anti-rat IgG Fc antibody conjugated with HRP using standard assay conditions. The ELISA plates were developed and mAb concentrations were calculated based on OD reading of the samples based on a standard curve with known rat IgG concentrations. ELISA assay results revealed that the recombinant rat IgG antibody was expressed at high levels in the supemutant of 293T cells transfected with the AAV plasmid containing a 2A sequence (FIG. 4).

The biological activity of the antibody was evaluated for neutralizing activity in a VEGF-FLK-1 binding assay. In this assay, recombinant VEGF (vascular endothelial cell growth factor, from R & D Systems) was coated on ELISA plates (Nunc), then blocked with 5% milk. The rat anti-FLK-1 antibody was pre-incubated at various concentrations with recombinant FLK-1-Fc (R & D Systems). The antibody/FLK-1 mixture was transferred to ELISA wells and the plates were incubated to allow VEGF-FLK-1 binding. After rinsing with balance solution, a goat anti-FLK-1 antibody conjugated with biotin was used to detect bound FLK-1, which was visualized by streptavidin-HRP (PharMingen) after color development using the HRP substrate.

Figure 5:
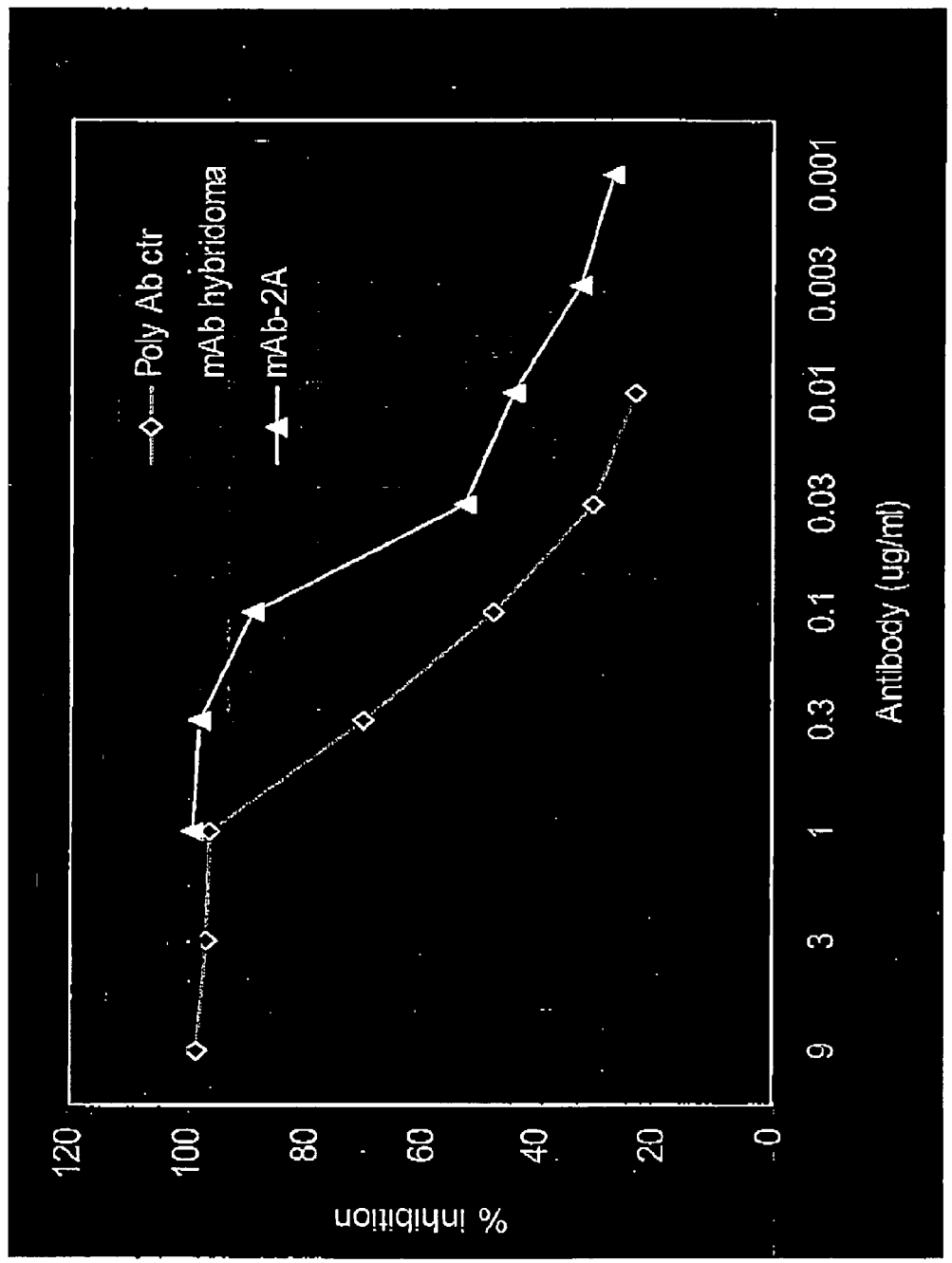
FIG. 5 demonstrates the biological activity of an anti-FLK-1 monoclonal antibody produced by 293 T cells transfected with the anti-FLK-1 IgG H2AL plasmid.

By way of the VEGF/FLK-1 (ligand-receptor) binding assay, it was demonstrated that the antibody expressed from 293T cells following transient transfecton exhibits full biological activity, similar to that of the native antibody expressed by the parental hybridoma cells (FIG. 5).

The antibody expressed utilizing the 2A sequence was further characterized by Western blot analysis. Protein in the supemutant of transiently transfected 293T cells (transfected with AAV H2AL plasmid) or from the supemutant of the parental hybridoma cells was separated by polyacrylamide gel electrophoresis under reducing or non-reducing conditions. For the reducing gel, protein samples were mixed with 2x LDS sample buffer (Invitrogen), boiled, loaded on pre-cast 12% Tris-Glycine gel (Invitrogen), and run with Tris-Glycine SDS running buffer. For the non-reducing gel, protein samples were mixed with 2x native TrisGly sample buffer (Invitrogen), loaded on pre-cast 12% Tris-Glycine gel (Invitrogen), and run with Tris-Glycine native running buffer (Invitrogen). After electrophoresis, the proteins were transferred to nitrocellulose membranes in Tris-Glycine transfer buffer with 20% methanol. The membranes were blocked with blocking solution and stained with HRP-conjugated ant-rat IgG. The membrane blots were treated with SuperSignal West Chemiliminescent substrate kit (Pierce) and protein bands were visualized using Biome film (Kodak).

Figure 6:
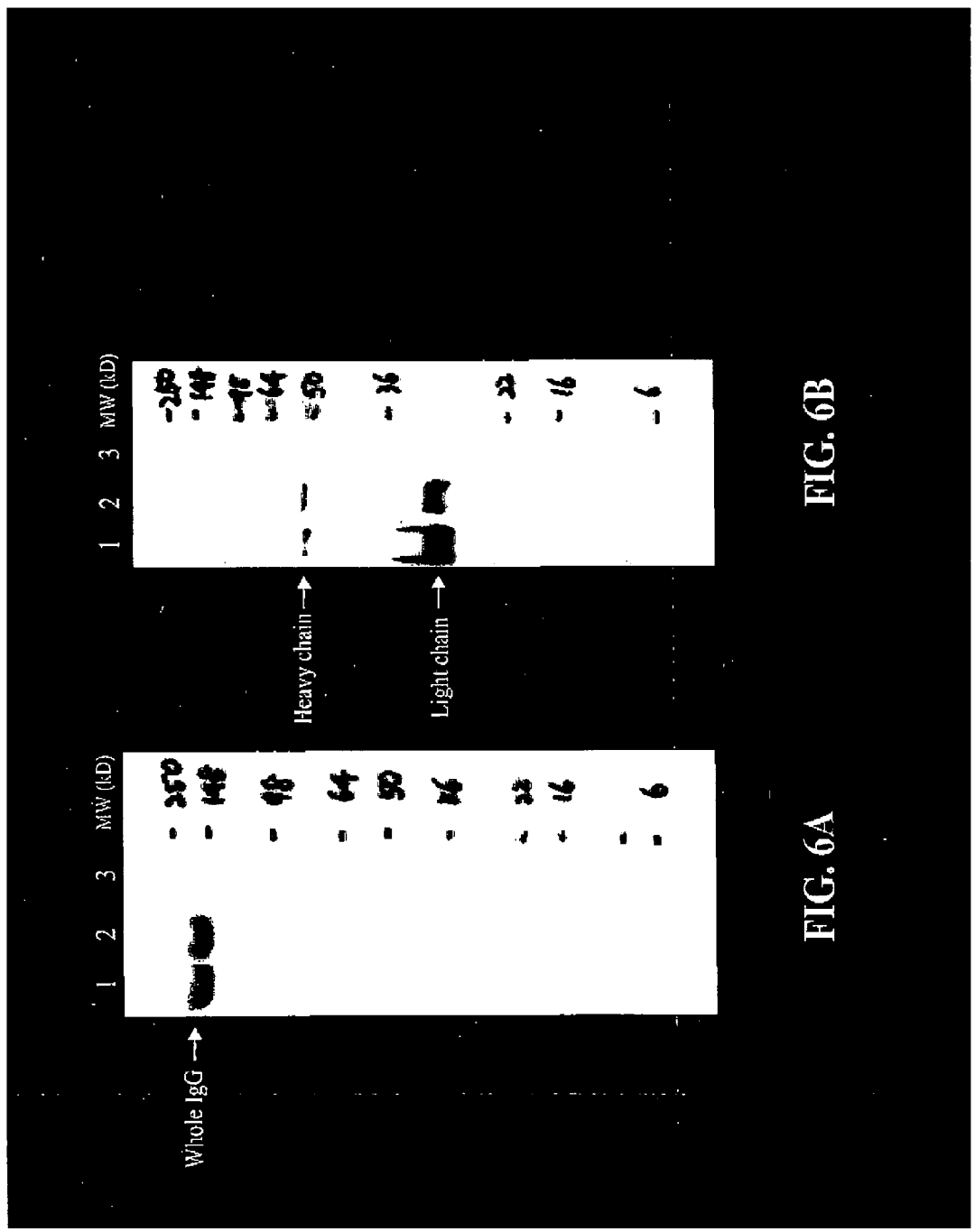

Western blot analysis revealed that the antibodies from both the parental hybridoma cell line and the transfected 293T cells appear as an approximately 160 kD bands on a non-reducing gel. This indicates that the heavy and light chains generated via the 2A cleavage site dimerized properly with the heavy and light chain ratio of 1:1, given that no additional bands (such as an approximately 133 kD band which would indicate a heavy to light chain ratio of 2:1), were visible. On a reducing gel, the antibodies from both hybridoma and transfected 293T cells appeared as an approximately 55 kD band (heavy chain) and a 23 kD band (light chain). No uncleaved 78 kD precursor polyprotein was detected, indicating efficient cleavage by the 2A peptide (FIG. 6B). Antibody expressed from the H2AL construct appeared slightly larger in molecular weight, presumably due to additional amino acid residues from the 2A sequence.

These results demonstrate that the 2A sequence provided a "cleavage" side facilitating the generation of both chains of the IgG molecule during the translation process in 293T cells. The chimeric H2AL polyprotein underwent autolytic cleavage to yield upon dimerization a full length, intact antibody (Ig) with two heavy and light chains.

EXAMPLE 3

Expression of a Human Immunoglobulin from an AAV H2AL Construct

In another example of the invention, the AAV 2A construct was used to express the heavy and light chain of a human monoclonal antibody to KDR. An AAV vector that encodes a novel human anti-VEGFR2 (KDR) mAb heavy chain, 2A, and light chain was constructed using the same strategy as described in Example 1. The AAV vector contains an EF1-alpha or CAG promoter, WPRE, and poly A sequence. 293T cells were transfected with the AAV plasmid by Fugen 6 kit as in Example 1 and cell supematants were harvested 72 hours post-transfection. The concentrations of the mAb in 293T cell supematants were determined using a sandwich ELISA assay from Bethyl Laboratories. In this assay, human IgG was captured by an immobilized anti-human IgG antibody on ELISA plates and detected by an anti-human IgG Fc antibody conjugated with HRP. Color was developed after adding substrate solution to the wells and mAb concentrations were calculated based on OD reading of the samples with the human IgG of known concentrations as a standard curve.

Figure 7:
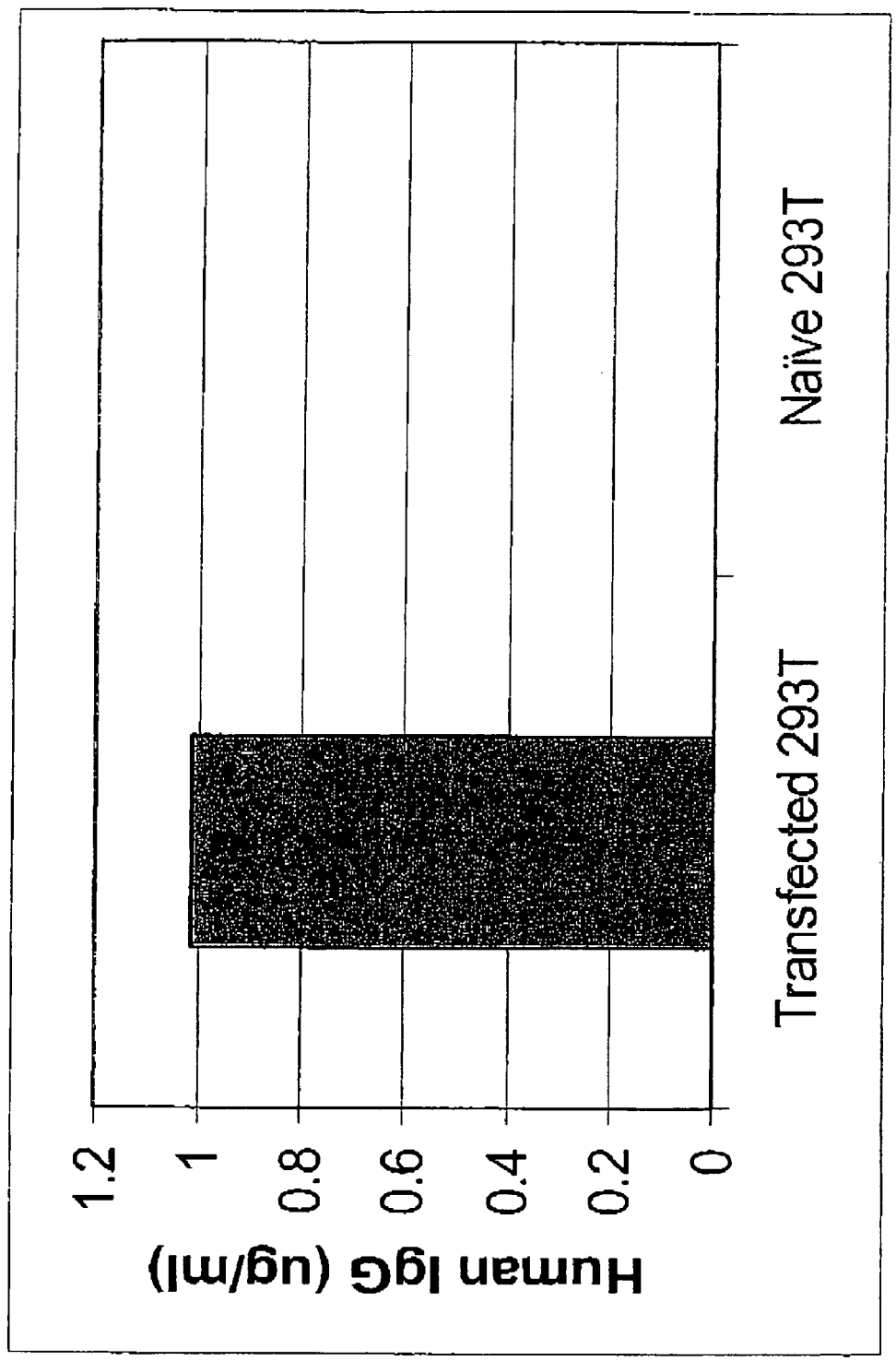
FIG. 7 demonstrates the expression of human anti-KDR monoclonal antibody (IgG) in the supernatant of 293T cells transfected with anti-KDR Ig/MV H2AL plasmid.

The results demonstrate that transfection of the AAV plasmid encoding the heavy and light chains of the human antibody linked by a 2A sequence into 293T cells resulted in high levels of full length antibody in cell culture supematants (FIG. 7). Therefore, antibody heavy and light chains can be generated from a single open reading frame through 2A sequence autocleavage. Furthermore, the heavy and light chains are folded and secreted properly.

EXAMPLE 4

Expression of Rat Anti-FLK-1 MAB from an AAV H2AL Vector in Nude Mice via Plasmid Hydrodynamic Gene Transfer This experiment serves to demonstrate that high level antibody expression can be achieved in the serum of mice transduced with an AAV plasmid that encodes an rat anti-FLK-1 mAb heavy and light chain linked by the FMDV 2A sequence. The AAV plasmid was constructed as described in the Examples 1 and 2 and expression of the transgene was driven by an EF1-alpha promoter. The plasmid was purified with Qiagen's Mega plasmid DNA purification kit according to the manufacture's instructions. The plasmid DNA was dissolved in PBS at 25 µg/ml and injected into NCR nu/nu mice via tail veins by hydrodynamic gene transfer at a flow rate of 1 ml/10 g body weight within 10 seconds. Hydrodamic gene delivery is described in Zhang et al., Human Gene Ther., 10:1735-1737, 1999 and Liu et al., Gene Ther., 6:1258-1266, 1999. Orbital sinus blood was collected at day 3, 10 and 17.

Figure 8:
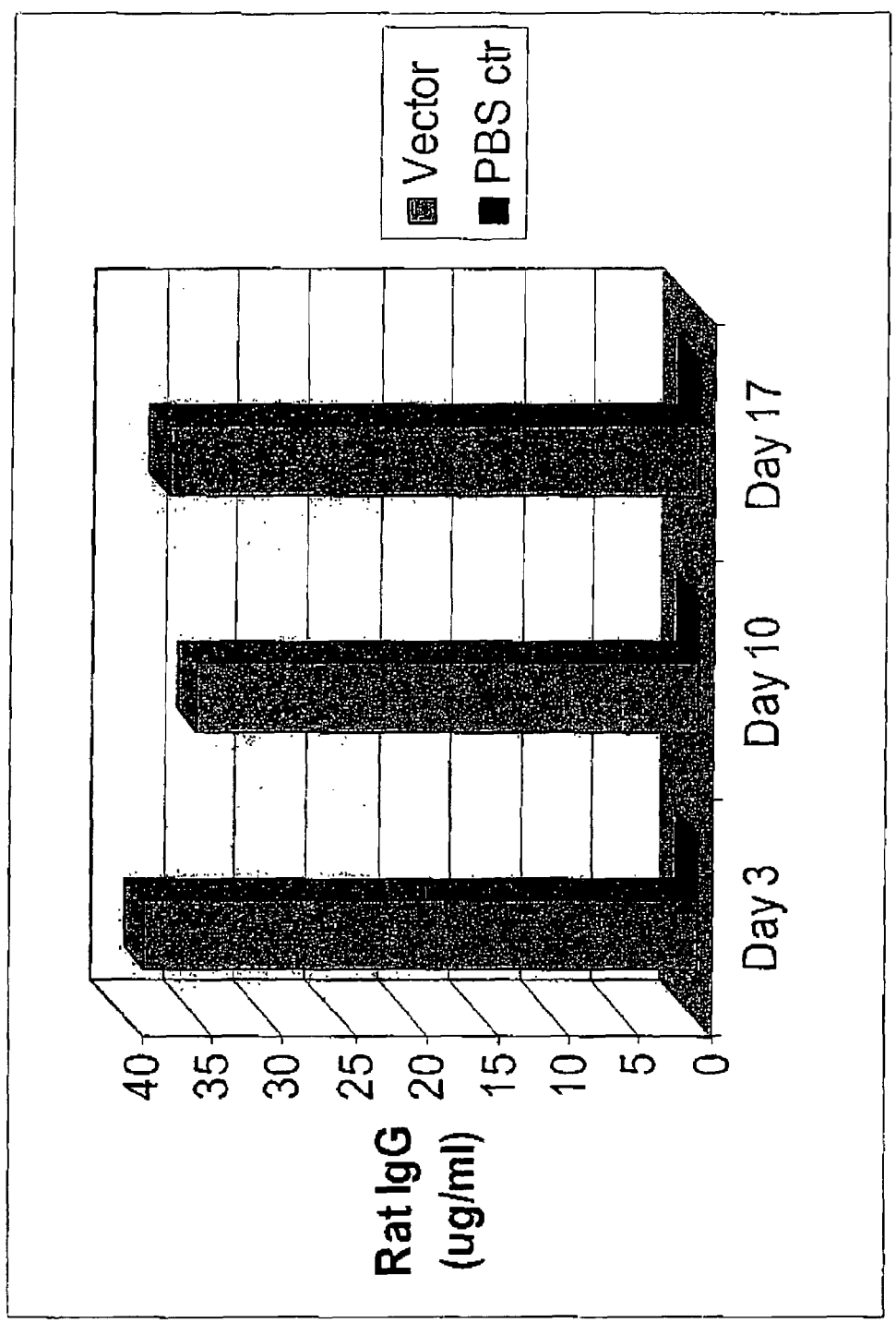
FIG. 8 demonstrates the expression of rat anti-FLK-1 antibody (IgG) in mouse sera following hydrodynamic gene transfer (also termed hydrodynamic application) of an anti-FLK-1 Ig/AAV H2AL plasmid in vivo.

The sera from the mice injected with the plasmid DNA or a PBS control were analyzed for antibody concentrations using a rat IgG kit as described in Example 2. High level expression of the rat mAb was detected in mouse sera. In contrast, no rat antibody was present when PBS only was injected (FIG. 8).

Figure 9:
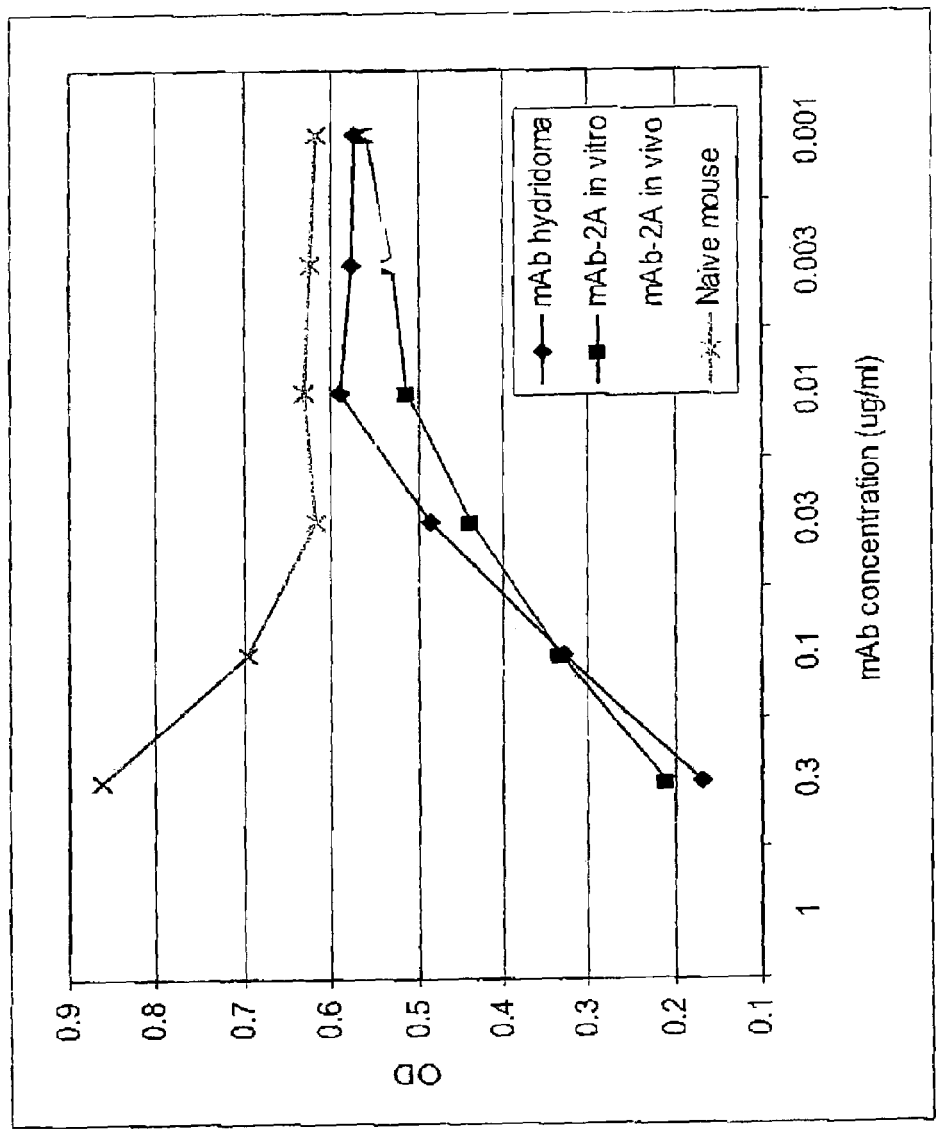
FIG. 9 demonstrates the biological activity of rat anti-FLK-1 IgG expressed in mouse sera following in vivo gene transfer (by hydrodynamic application) with an anti-FLK-1 Ig/AAV H2AL plasmid.

Furthermore, it was shown that the antibody expressed in mouse serum retained biological activity, comparable to the antibody expressed from the parental hybridoma cells, as determined by the neutralizing effect of the antibody in the VEGF-FLK-1 binding assay described in Example 2 (FIG. 9).

Figure 10:
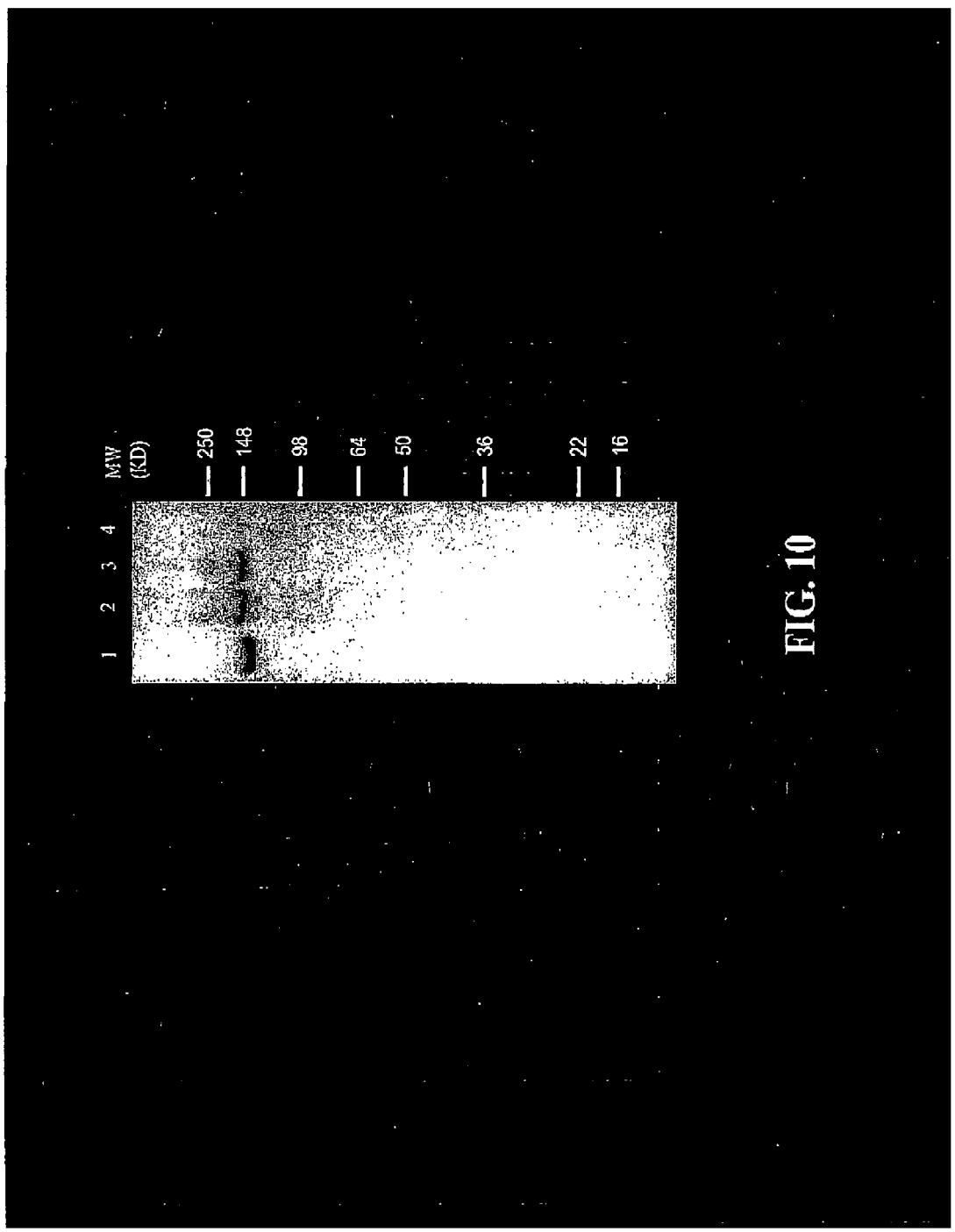
FIG. 10 depicts the results of Western blot analysis of rat anti-FLK-1 immunoglobulin in mouse sera following in vivo gene transfer of an anti-FLK-1 Ig/MV H2AL construct following PAGE using a 12% native gel, wherein Lane 1 shows IgG expressed from hybridoma cells; Lane 2 shows IgG expressed using a 2A sequence in vitro; Lane 3 shows IgG expressed using a 2A sequence in mouse sera following in vivo gene transfer; and Lane 4 is naive mouse sera.

To evaluate the cleavage efficiency of the 2A sequence and the molar ratio of the antibody heavy and light chains expressed in vivo, IgG from the mouse sera injected with or without vector was separated on a 12% Tris-Glycine gel under non-denaturing conditions, as described in Example 2. The separated proteins were transferred onto nitrocellular membranes using the Western blot procedure described in Example 2. As shown in FIG. 10, a protein band at approximately a 160 kD was observed in the serum of mice injected with the AAV H2AL vector, but not in the serum of control mice injected with PBS. This size is consistent with the expected molecular weight of the antibody under non-denaturing conditions, which is composed of two antibody heavy chains and two light chains following dimerization. This rat IgG band migrates at the same rate and hence is the same size as the antibody (IgG) expressed using constructs comprising the 2A sequence from transiently transfected 293T cells (as detailed in Example 2) and is slightly bigger than the IgG expressed from the parental hybridoma cells presumably due to the additional amino acid residues derived from the 2A sequence or postranslational modifications.

Taken together, the results demonstrate that full-length functional antibodies can be expressed at high levels in vivo from an AAV vector driving a single open reading frame of an immunoglobulin heavy and light chain cDNA from a single promoter when provided with a self processing (2A) cleavage sequence between the two chains.

The self processing cleavage sequence facilitates efficient cleavage of the two peptides. The antibody heavy and light chains are properly folded and secreted, and form a functional antibody with biological activity as potent as the original monoclonal antibody (mAb) produced by the parental hybridoma cells. The secreted antibody forms proper homodimers between two heavy chain peptides and heterodimers between a heavy and a light chain with an apparent 1:1 ratio as judged by a single band in a non-reducing protein gel.

EXAMPLE 5

Figure 11:
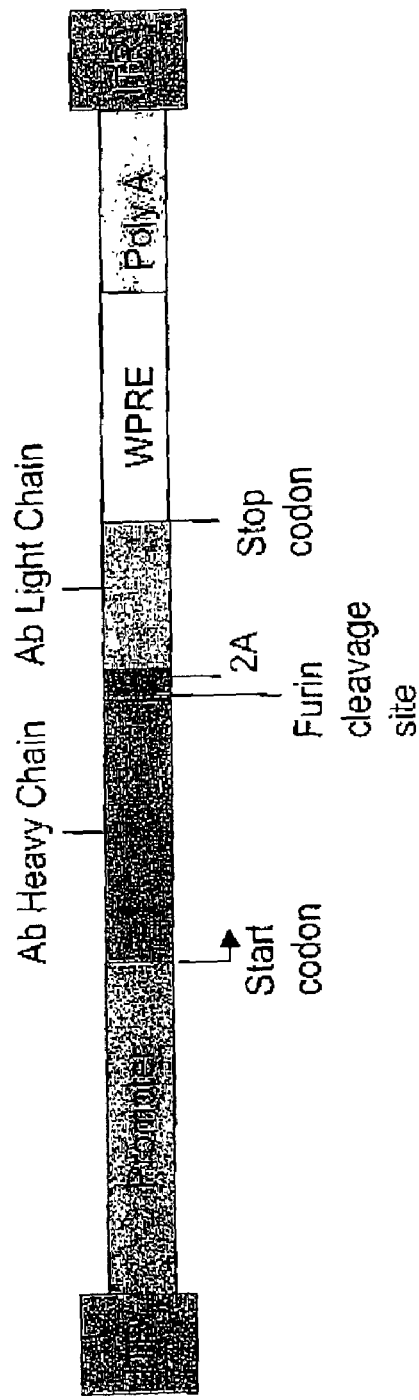
FIG. 11 depicts an MV expression cassette encoding an antibody heavy chain, a furin cleavage site, a 2A sequence, and an antibody light chain (HF2AL) for a rat anti-FLK-1 antibody.

Removal of 2A Cleavage Site Residues from Antibodies Expressed via an AAV HF2AL Vector Antibody heavy chains expressed using the H2AL constructs described above carry amino acid residues derived from the self processing cleavage sequence such as a 2A or 2A-like sequence at their C-terminus, which remain following self cleavage. To further optimize the expression system, a vector was constructed which includes a protease cleavage site between the first polypeptide, i.e. the antibody heavy chain in this particular construct, and the 2A sequence. The cleavage site used in the construct was RAKR (SEQ ID NO: 11), which belongs to the category of furin consensus cleavage sequences. Expected cleavage occurs between A and K in this cleavage site by furin or other proteases. The construct consists of in the 5' to 3' direction: a CAG promoter, the antibody heavy chain coding sequence, a furin cleavage site coding sequence, the 2A cleavage site coding sequence, the antibody light chain coding sequence, and a polyA sequence (CAG HF2AL) (FIG. 11).

Figure 12:
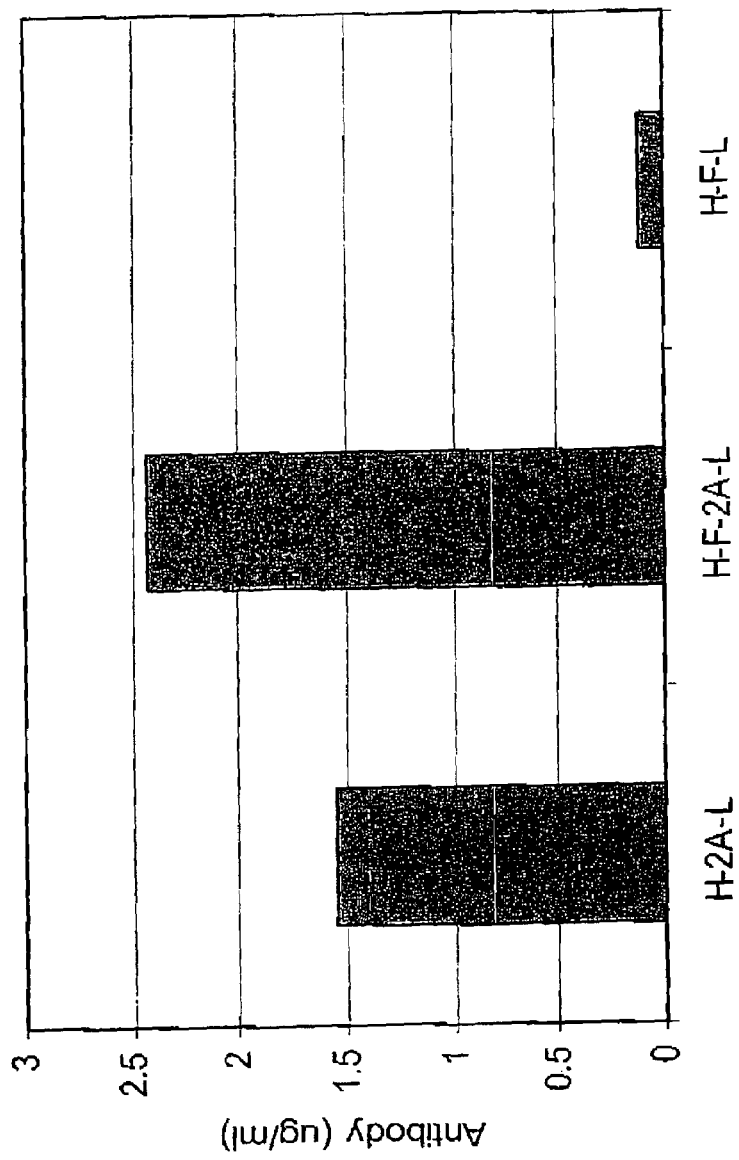
FIG. 12 depicts rat anti-FLK-1 antibody expression in 293T cells transfected with MV HF2AL and MV H2AL plasmids.

To express the antibody from the CAG HF2AL construct, plasmid DNA was purified using a Qiagen plasmid DNA purification kit and used to transfect 293T cells in 6 well tissue culture plates using the FuGENE 6 kit (Roeche). The next day, cells were fed with serum-free medium and the conditioned media were harvested after 48 hours. In one control experiment, 293T cells were transfected with H2AL plasmid, which contains the same antibody and 2A sequence but lacks the furin cleavage site between the heavy chain and the 2A sequence. In the second control experiment, 293T cells were transfected with HFL plasmid, which contains the antibody heavy chain, the furin cleavage site, and the antibody light chain, but lacks the 2A sequence. Antibody concentrations in conditioned media were determined by ELISA. As shown in FIG. 12, the HF2AL construct gave higher antibody expression levels in supernatants from transfected cells than the H2AL construct. On the other hand, only very limited amount of antibody was detected in 293T cell supernatant transfected with the HFL construct.

Figure 13:
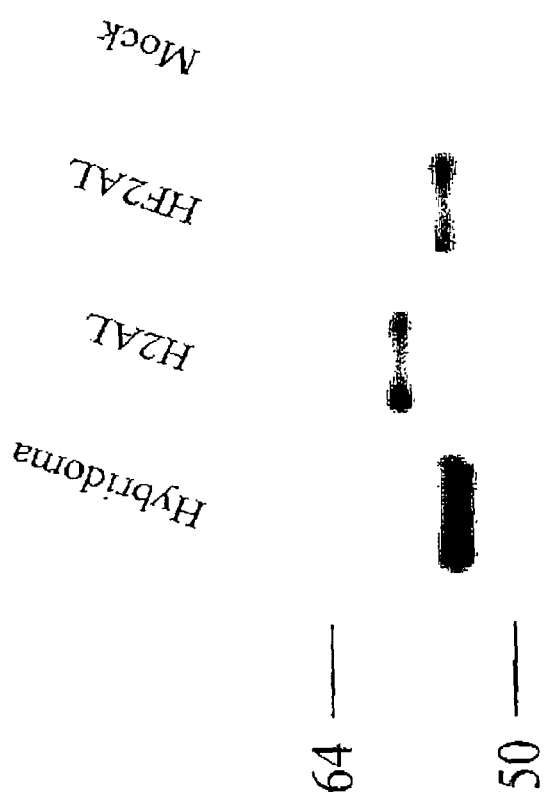
FIG. 13 depicts the results of a Western blot analysis showing the relative expression of rat anti-FLK-1 antibody heavy chain from hybridoma cells as compared to 293T cells transfected with an HF2AL or H2AL plasmid.

To evaluate the efficiency of the furin cleavage site to remove the additional 2A amino acid residues from the heavy chain of the antibody, antibodies in supernatants of HF2AL and H2AL transfected cells were separated in a 12% Tris-Glycine SDS-PAGE gel under reducing conditions. The separated proteins were transferred onto a nitrocellulose membrane and the protein band for the antibody heavy chain was detected by a rabbit anti-rat antibody. This Western blot analysis showed that the antibody heavy chains expressed from the HF2AL plasmid migrated as a single band at a molecular weight that was smaller than the heavy chains expressed from the H2AL construct but similar to the antibody heavy chains expressed by parental hybridoma cells (FIG. 13). This result suggests that the furin cleavage site within the HF2AL construct provides an efficient means to remove residual 2A derived amino acids.

EXAMPLE 6

Expression of Antibodies in Furin −/− Cells Following Transfection with AAV Plasimids Containing a 2A Site and Furin Cleavage Site Furin is a ubiquitous subtilisin-related serine protease that is expressed in almost all cell types. Two cell lines, LoVo and CHO mutant RPE.40, have been found to have no functional furin due to mutations. Given that the furin cleavage site RAKR used in the CAG HF2AL construct (Example 5) can be cleaved by furin as well as many other members of proteases in the same family, an experiment was conducted to identify the actual enzyme responsible for the cleavage of RAKR in the antibody expressed from the CAG HF2AL construct. Plasmids with or without a furin cleavage site (HF2AL or H2AL) were used to transfect LoVo cells. LoVo is a human colon carcinoma cell line with no functional furin due to one nucleotide deletion in the region covering the homo B domain essential for the endoproteolytic activity to RXK(R)R (Takahashi et al., Biochem Biophys Res Commun. 195:1019-26.(1993)).

Figure 14:
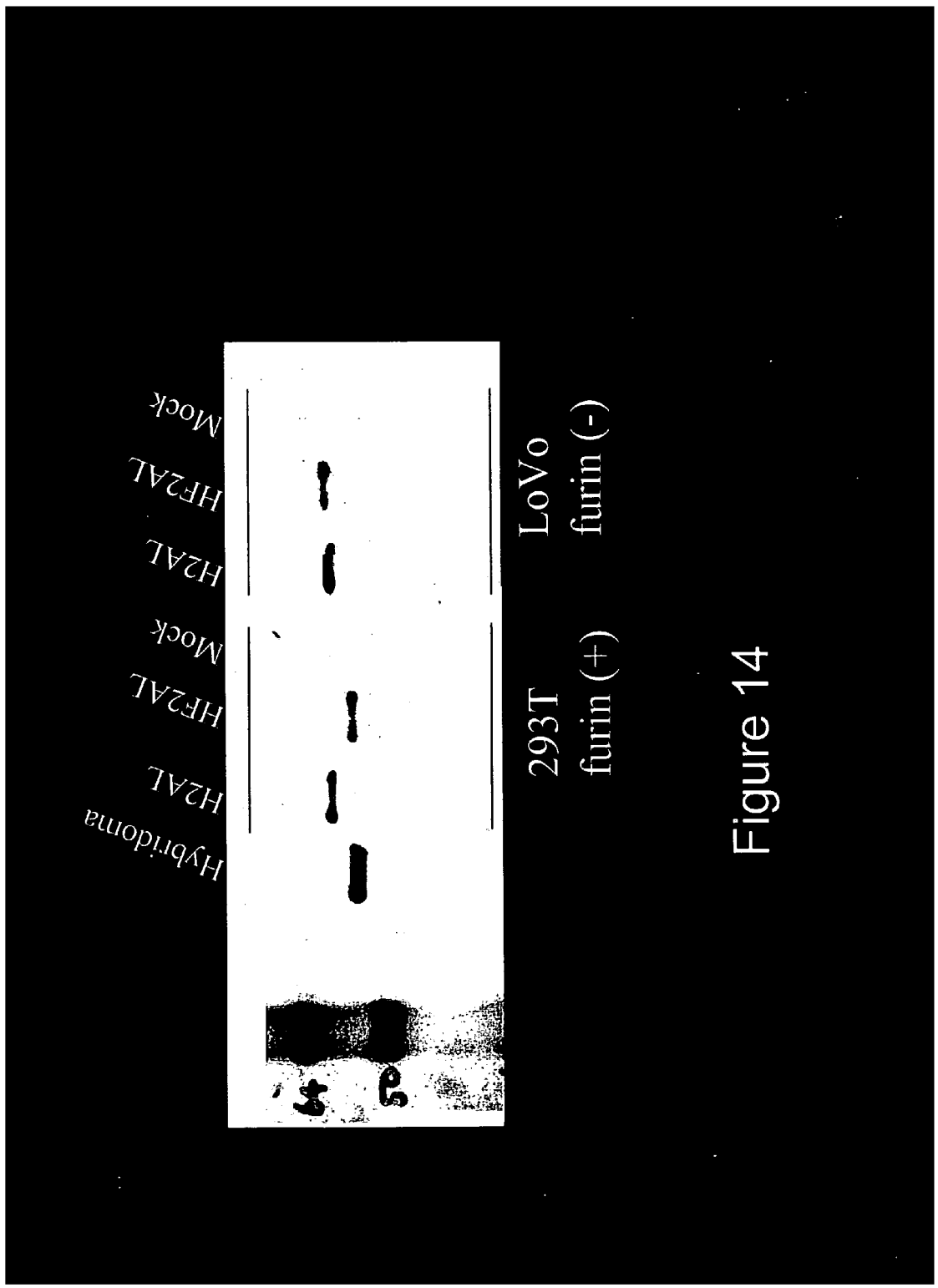
FIG. 14 shows Western blot characterization of an antibody heavy chain expressed from 293T (furin+) and LoVo (furin−) cells transfected with H2AL and HF2AL constructs as described in Example 6 and 7.

Following HF2AL and H2AL plasmid transfection into LoVo cells using the FuGENE 6 kit, cell culture supernatants were harvested from tissue culture dishes. Proteins were separated in a 12% Tris-Glycine SDS-PAGE gel under reducing conditions and analyzed in Western blot analysis, as described in Example 2. Results showed that the antibody heavy chains expressed from the HF2AL plasmid migrated at a molecular weight similar to the heavy chains expressed from the H2AL construct but higher than the antibody heavy chain expressed by parental hybridoma cells (FIG. 14). These results demonstrate that in LoVo cells which lack furin activity, additional amino acids derived from the 2A cleavage site remain at the C-terminus of the antibody heavy chain, confirming that the protease furin is the actual enzyme responsible for removal of 2A residues from the antibody when expressed in furin containing cells, such as 293T cells.

To further confirm the removal of residual aminoacids from the 2A peptide sequence at the C terminus of the heavy chain expressed from the HF2A vector, the C-terminal fragment of the antibody heavy chain was analyzed by mass spectrum analysis. An expression vector was constructed that contains the rat antibody heavy chain, a furin cleavage site adjacent to the 2A cleavage site (RAKR), the antibody light chain, and 6 his amino acids (HF2AL 6H), called "His-Tag". The plasmid was injected into mice via hydrodynamic gene transfer as described in Example 4. The his-tagged monoclonal antibody was purified from mouse serum under native conditions using a Nickel column (Qiagen). The antibody heavy and light chains were separated on a 10% SDS-PAGE gel stained with Coomassie blue. The antibody heavy chain band was isolated from the SDS-PAGE gel and subjected to mass spectrum analysis after trypsin digestion. Mass spectrum data confirmed the removal of all but two amino acids derived from the 2A/furin sequences at the C terminus of the antibody heavy chain. Furthermore, by using combination of mass spectrum and PSD (MS/MS) sequencing analyses, it could be shown that the antibody heavy chain expressed from the HF2AL construct has the C-terminal sequence "SLSH-SPGKRA" (SEQ ID NO: 14), which includes native rat IgG heavy chain C-terminal amino acids plus two additional amino acids (RA) derived from the furin cleavage site.

In summary, our studies demonstrate that residual 2A sequence derived amino acids attached to the protein that is located at the 5' end of the 2A sequence can be efficiently removed during protein expression and secretion by introducing an additional proteolytic cleavage site (i.e., a furin cleavage site) adjacent the 2A cleavage site. Removal of 2A sequence derived amino acids results in generation of a product lacking foreign sequences which may otherwise elicit immune responses when used in vivo. Furthermore, these data also suggest that the addition of a furin cleavage site in 2A containing constructs results in overall improved antibody expression levels, presumably due to improved antibody secretion upon removal of 2A residues.

What is claimed is:

1. A vector for expression of a recombinant immunoglobulin or a recombinant immunoglobulin fragment having antigen-binding activity, wherein the immunoglobulin fragment is selected from the group consisting of Fab, F(ab')$_2$, and Fv(scFV) immunoglobulin fragments, the vector comprising: in the 5' to 3' direction, a promoter operably linked to all of (1) a coding sequence for a heavy chain of the immunoglobulin or a fragment of the heavy chain, (2) a sequence encoding a furin cleavage site, (3) a sequence encoding a 2A self-processing cleavage site, and (4) a coding sequence for a light chain of the immunoglobulin or a fragment of the light chain.

2. The vector according to claim 1, wherein the vector is selected from the group consisting of an adeno-associated virus (AAV) vector, a lentivirus vector, a retrovirus vector, a replication competent adenovirus vector, a replication deficient adenovirus vector, a gutless adenovirus vector, a herpes virus vector and a nonviral plasmid.

3. The vector according to claim 2, wherein said vector is an adeno-associated virus (AAV) vector.

4. The vector according to claim 1, wherein the 2A self-processing cleavage site is selected from the group consisting of SEQ ID NO: 1, SEQ ID NO: 2 and SEQ ID NO: 9.

5. The vector according to claim 1, wherein the 2A self-processing cleavage site is SEQ ID NO: 6.

6. The vector according to claim 5, wherein the sequence encoding the furin cleavage site encodes an oligopeptide with the consensus sequence RXK(R)R (SEQ ID NO: 10).

7. An isolated host cell transfected with the vector of claim 6.

8. The vector according to claim 1, wherein the coding sequence for the heavy chain of the immunoglobulin is the full length coding sequence of the immunoglobulin heavy chain.

9. The vector according to claim 1, wherein the sequence encoding the furin cleavage site encodes an oligopeptide with the consensus sequence RXK(R)R (SEQ ID NO: 10).

10. An insolated host cell transfected with the vector of claim 9.

11. The vector according to claim 1, wherein the promoter is selected from the group consisting of an elongation factor 1-alpha promoter (EF1α) promoter, a phosphoglycerate kinase-1 promoter (PGK) promoter, a cytomegalovirus immediate early gene promoter (CMV), a chimeric liver-specific promoter (LSP), a cytomegalovirus enhancer/chicken beta-actin promoter (CAG), a tetracycline responsive promoter (TRE), a transthyretin promoter (TTR), a simian virus 40 promoter (SV40) and a CK6 promoter.

12. The vector according to claim 1, further comprising a signal sequence 5' to the coding sequence for the heavy chain of the immunoglobulin or the fragment of the heavy chain, or the coding sequence for the light chain of the immunoglobulin or the fragment of the light chain.

13. The vector according to claim 1, wherein the heavy chain of the immunoglobulin or the fragment of the heavy chain and the light chain of the immunoglobulin or the fragment of the light chain are expressed in an equimolar ratio.

14. A vector for expression of a recombinant immunoglobulin or a recombinant immunoglobulin fragment having antigen-binding activity, wherein the immunoglobulin fragment is an Fv immunoglobulin fragment, the vector comprising:
  in the 5' to 3' direction, a promoter operably linked to all of (1) a coding sequence for a heavy chain of the immunoglobulin or a fragment of the heavy chain (2) a sequence encoding a furin cleavage site, (3) a sequence encoding a 2A self-processing cleavage site, and (4) a coding sequence for a light chain of the immunoglobulin or a fragment of the light chain.

15. The vector according to claim 14, wherein the vector is selected from the group consisting of an adeno-associated virus (AAV) vector, a lentivirus vector, a retrovirus vector, a replication competent adenovirus vector, a replication deficient adenovirus vector, a gutless adenovirus vector, a herpes virus vector and a nonviral plasmid.

16. The vector according to claim 15, wherein said vector is an adeno-associated virus (AAV) vector.

17. The vector according to claim 14, wherein the 2A self-processing cleavage site is selected from the group consisting of SEQ ID NO: 1, SEQ ID NO: 2, SEQ ID NO: 6 and SEQ ID NO: 9.

18. The vector according to claim 17, wherein the sequence encoding the furin cleavage site encodes an oligopeptide with the consensus sequence RXK(R)R (SEQ ID NO: 10).

19. An isolated host cell transfected with the vector of claim 18.

20. The vector according to claim 14, wherein the coding sequence for the heavy chain of the immunoglobulin is the full length coding sequence of the immunoglobulin heavy chain.

21. The vector according to claim 14, wherein the sequence encoding the furin cleavage site encodes an oligopeptide with the consensus sequence RXK(R)R (SEQ ID NO:10).

22. An isolated host cell transfected with the vector of claim 21.

23. The vector according to claim 14, wherein the promoter is selected from the group consisting of an elongation factor 1-alpha promoter (EF1α) promoter, a phosphoglycerate kinase-1 promoter (PGK) promoter, a cytomegalovirus immediate early gene promoter (CMV), a chimeric liver-specific promoter (LSP), a cytomegalovirus enhancer/chicken beta-actin promoter (CAG), a tetracycline responsive promoter (TRE), a transthyretin promoter (TTR), a simian virus 40 promoter (SV40) and a CK6 promoter.

24. The vector according to claim 14, further comprising a signal sequence 5' to the coding sequence for the heavy chain of the immunoglobulin or the fragment of the heavy chain, or the coding sequence for the light chain of the immunoglobulin or the fragment of the light chain.

25. The vector according to claim 14, wherein the heavy chain of the immunoglobulin or the fragment of the heavy chain and the light chain of the immunoglobulin or the fragment of the light chain are expressed in an equimolar ratio.

26. A method for producing a recombinant immunoglobulin or a recombinant immunoglobulin fragment having antigen-binding activity, wherein the immunoglobulin fragment is selected from the group consisting of Fab, F(ab')$_2$, Fv, and Fv(scFV) immunoglobulin fragments, comprising the steps of:
  (i) introducing a vector for expression of the recombinant immunoglobulin or the recombinant immunoglobulin fragment into a single host cell, said vector comprising:
    in the 5' to 3' direction, a promoter operably linked to all of (1) a coding sequence for a heavy chain of the immunoglobulin or a fragment of the heavy chain, (2) a sequence encoding a furin cleavage site, (3) a sequence encoding a 2A self-processing cleavage site and (4) a coding sequence for a light chain of the immunoglobulin or a fragment of the light chain; and
  (ii) expressing the heavy chain of the immunoglobulin or the fragment of the heavy chain and the light chain of the immunoglobulin or the fragment of the light chain in said transformed single host cell, wherein the heavy chain of the immunoglobulin or the fragment of the heavy chain and the light chain of the immunoglobulin or the fragment of the light chain are expressed in an equimolar ratio.

27. The method according to claim 26, wherein the 2A self-processing cleavage site is selected from the group consisting of SEQ ID NO:1, SEQ ID NO:2, SEQ ID NO:6 and SEQ ID NO:9.

28. The method according to claim 26, wherein the sequence encoding the furin cleavage site encodes an oligopeptide with the consensus sequence RXK(R)R (SEQ ID NO: 10).

* * * * *